(12) United States Patent
Deisseroth et al.

(10) Patent No.: US 11,839,655 B2
(45) Date of Patent: Dec. 12, 2023

(54) COMBINATION CANCER THERAPY

(71) Applicant: MicroVAX, LLC, Warrenton, VA (US)

(72) Inventors: Albert B. Deisseroth, Potomac, MD (US); Nagy Habib, London (GB)

(73) Assignee: MicroVAX, LLC, Warrenton, VA (US)

( * ) Notice: Subject to any disclaimer, the term of this patent is extended or adjusted under 35 U.S.C. 154(b) by 33 days.

(21) Appl. No.: 15/882,181

(22) Filed: Jan. 29, 2018

(65) Prior Publication Data

US 2019/0070289 A1  Mar. 7, 2019

Related U.S. Application Data

(60) Provisional application No. 62/595,106, filed on Dec. 6, 2017, provisional application No. 62/562,636, filed on Sep. 25, 2017, provisional application No. 62/553,363, filed on Sep. 1, 2017.

(51) Int. Cl.
| | |
|---|---|
| *A61P 35/00* | (2006.01) |
| *A61K 39/395* | (2006.01) |
| *C07K 16/28* | (2006.01) |
| *A61K 39/00* | (2006.01) |

(52) U.S. Cl.
CPC .... *A61K 39/39558* (2013.01); *A61K 39/0011* (2013.01); *A61K 39/00117* (2018.08); *A61K 39/39541* (2013.01); *A61P 35/00* (2018.01); *C07K 16/2803* (2013.01); *C07K 16/2818* (2013.01); *C07K 16/2827* (2013.01); *A61K 2039/505* (2013.01); *A61K 2039/53* (2013.01); *A61K 2039/54* (2013.01); *A61K 2039/545* (2013.01); *A61K 2039/6031* (2013.01); *C12N 2710/10043* (2013.01)

(58) Field of Classification Search
CPC ............................................... A61K 39/39558
USPC ..................................................... 424/155.1
See application file for complete search history.

(56) References Cited

U.S. PATENT DOCUMENTS

| | | | |
|---|---|---|---|
| 8,119,117 B2 | 2/2012 | Deisseroth et al. | |
| 8,299,229 B2 | 10/2012 | Tang et al. | |
| 8,828,957 B2 | 9/2014 | Deisseroth et al. | |
| 9,533,036 B2 | 1/2017 | Tang et al. | |
| 2015/0064209 A1* | 3/2015 | Deisseroth | A61K 39/0011 424/192.1 |
| 2015/0118222 A1* | 4/2015 | Levy | A61K 31/519 424/130.1 |
| 2017/0239339 A1 | 8/2017 | Deisseroth et al. | |

FOREIGN PATENT DOCUMENTS

| | | |
|---|---|---|
| JP | 2008504219 A | 2/2008 |
| WO | 2016197067 A1 | 12/2016 |
| WO | 2017139725 A1 | 8/2017 |

OTHER PUBLICATIONS

Shimizu et al (Invest New Drugs, 2016, 34: 347-354).*
Ribas et al (Cancer Immunol, Res, 2016, 4(3): 194-203).*
Hamanishi et al (Int J Clin Oncol, 2016, 21: 462-473).*
Guo et al (PLOS One, 2014, 9(2)(e89350) 10 pages).*
Mkrtichyan et al (Journal for Immunotherapy of Cancer, 2013, 1(15): 1-9).*
Curran et al (PNAS, 2010, 107(9): 4275-4280).*
Yu et al (Oncoimmunology, 2016, 5(6): e1151594 (12 pages)).*
Yu et al (Oncotarget , 2015, 6(39): 42067-42080).*
Topalian et al (Journal of Clinical Oncology, 2014, 32(10): 1020-1030).*
Kleponis et al (Cancer Biol Med, 2015, 12: 201-208).*
Soares et al (J Immunother, 2015, 38(1): 1-11).*
Rekoske et al (Cancer Immunol Res, 2015, 3(8): 946-955).*
Rice et al (Cancer Gene Therapy, 2015, 22: 454-462).*
Antonios et al (JCI Insight, 2016, 1(10): e87059).*
A. Deisseroth et al., TAA/ecdCD40L adenoviral prime-protein boost vaccine for cancer and infectious diseases, Cancer Gene Therapy, (2013) 20, pp. 65-69.
K. Thind et al., Immunotherapy in pancreatic cancer treatment: a new frontier, Therapeutic Advances in Gastroenterology 2017, vol. 10(1), pp. 168-194.
I. Mellman, Dendritic Cells: Master Regulators of the Immune Response, Cancer Immunology Research, Sep. 2013(1); 145, 6 pages.
Y. Tang et al., Multistep process through which adenoviral vector vaccine overcomes anergy to tumor-associated antigens, Blood, Nov. 1, 2004, vol. 104, No. 9, pp. 2704-2713.
Y. Tang et al., Use of CD40L immunoconjugates to overcome the defective immune response to vaccines for infections and cancer in the aged, Cancer Immunology Immunotherapy (2009) 58, pp. 1949-1957.
Y. Tang et al., Vector Prime/Protein Boost Vaccine That Overcomes Defects Acquired during Aging and Cancer, The Journal of Immunology vol. 177, 2006, pp. 5697-5707.
Z. Ye et al., Cancer vaccine: learning lessons from immune checkpoint inhibitors, Journal of Cancer 2018, vol. 9, pp. 263-268.
K. T. Byrne and R. H. Vonderheide, CD40 Stimulation Obviates Innate Sensors and Drives T Cell Immunity in Cancer, Cell Reports 15, Jun. 21, 2016, pp. 2719-2732.

(Continued)

*Primary Examiner* — Sean E Aeder
(74) *Attorney, Agent, or Firm* — Jacob Frank; Glenn Snyder; Snyder, Clark, Lesch & Chung, LLP

(57) ABSTRACT

A method and combination for treating a cancer patient by combining two distinct immuno-therapy solutions for administration to a patient within a common time period, comprising a checkpoint inhibitor antibody component such as a PD-1 or PD-L1 antibody administered by infusion, and a TAA/ecdCD40L vaccine component administered subcutaneously, wherein an initial antibody component administered is followed by at least several successive antibody boosts and an initial vaccine component administered is followed by at least several successive vaccine boosts, both the initial and boosts of each administered within at least said common time period, wherein the combined administration of said two distinct immuno-therapy solutions provides for an enhanced therapeutic effect, over that of the therapeutic effect of either of the two distinct immunotherapy component solutions when administered alone as monotherapy.

3 Claims, 20 Drawing Sheets

(56) References Cited

OTHER PUBLICATIONS

G. L. Beatty et al., CD40 Agonists Alter Tumor Stroma and Show Efficacy Against Pancreatic Carcinoma in Mice and Humans, Science, 331(6024), Mar. 25, 2011, 9 pages.

L. Zhang et al., An adenoviral vector cancer vaccine that delivers a tumor-associated antigen/CD40-ligand fusion protein to dendritic cells, PNAS, Dec. 9, 2003, vol. 100, No. 25, pp. 15101-15106.

F. Cappuccini et al., Immunogenicity and efficacy of the novel cancer vaccine based on simian adenovirus and MVA vectors alone and in combination with PD-1 mAb in a mouse model of prostate cancer, Cancer Immunology Immunotherapy, 2016, vol. 65, pp. 701-713.

J. Dine et al., Immune Checkpoint Inhibitors: An Innovation in Immunotherapy for the Treatment and Management of Patients with Cancer, Asia Pacific Journal of Oncology Nursing, Apr.-Jun. 2017, vol. 4(2), pp. 127-135.

International Search Report and the Written Opinion of the International Searching Authority issued for the corresponding international application No. PCT/US2018/048462, dated Dec. 27, 2018, 9 pages.

Claude-Agnes Reynaud et al., and Griffin et al., "Gene Profiling of CD11b+ and CD11b− B1 cell subsets reveals potential cell sorting artifacts," and "Human CD11b+ B1 cells are not monocytes: A reply to Gene Profiling of CD11b+ and CD11b− B1 cell subsets reveals potential cell sorting artifacts," The Journal of Experimental Medicine, Mar. 2012, vol. 209 No. 3, pp. 433-436.

A. Haslam, J. Gill, V. Prasad, Estimation of the Percentage of US Patients With Cancer Who Are Eligible for Immune Checkpoint Inhibitor Drugs. JAMA Network Open, Mar. 2020; 3(3): e200423. Published online Mar. 9, 2020, 3 pages.

MD Anderson launches James P. Allison Institute to usher in new era for immunotherapy, MD Anderson News Release Mar. 24, 2022, 3 pages.

C. Engblom, C. Pfirschke, M.J. Pittet. "The role of myeloid cells in cancer therapies," Nat. Rev. Cancer, Jul. 2016, 16(7), pp. 447-462.

M. C. Schmid et al. "Integrin CD11b activation drives anti-tumor innate immunity," Nature Communications, (2018) 9:5379 / DOI: 10.1038/s41467-018-07387-4, pp. 1-14.

Akbulut H., et al.. "Addition of adenoviral vector targeting of chemotherapy to the MUC-1/ecdCD40L VPPP vector prime protein boost vaccine prolongs survival of mice carrying growing subcutaneous deposits of Lewis lung cancer cells." Gene Therapy (2010) 17, pp. 1333-1340.

* cited by examiner

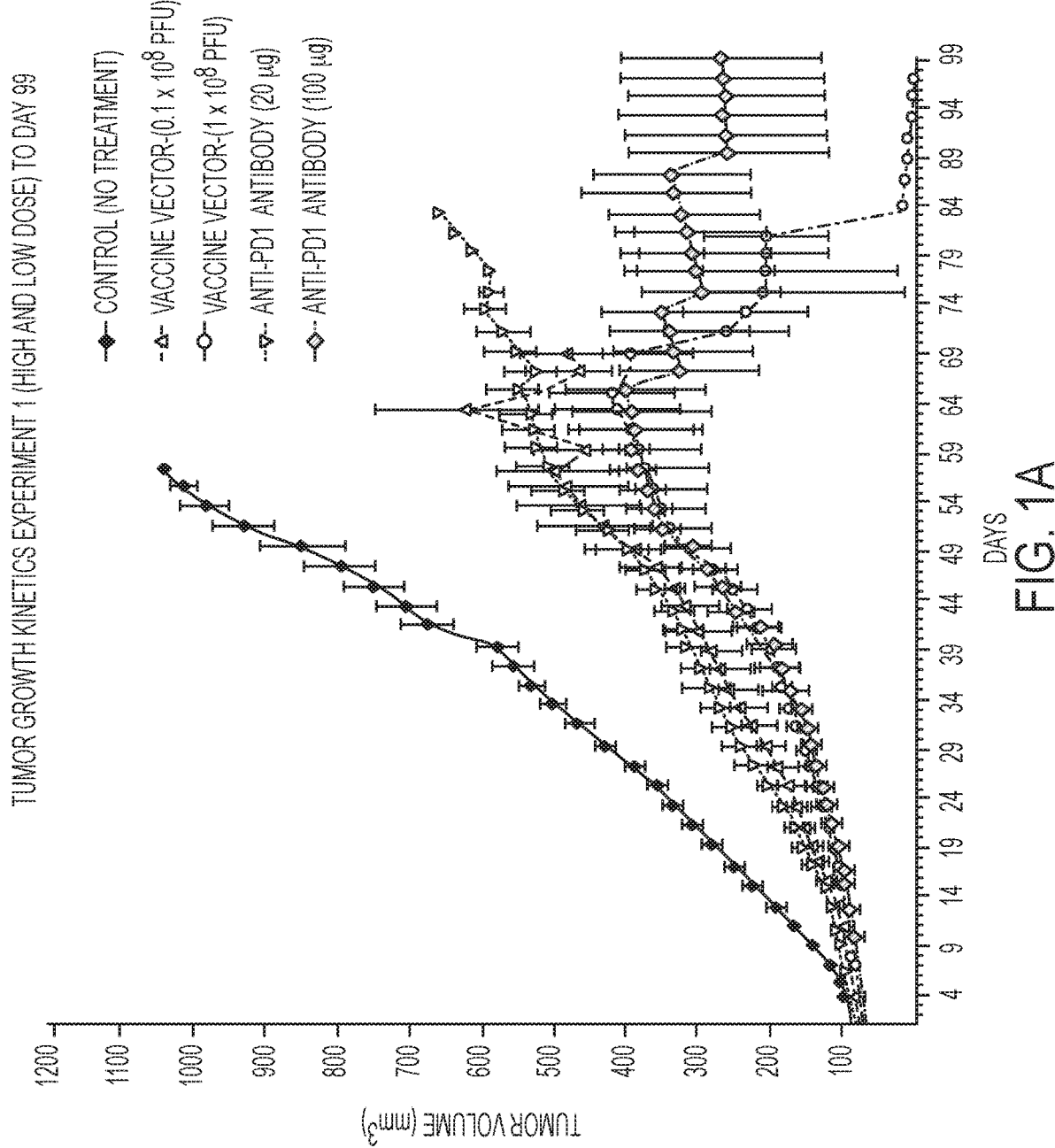

| GROUP | TUMOR VOLUME (mm³) DAY 57 MEAN ± SEM | %TGI (BY DELTA) DAY 55 |
|---|---|---|
| GROUP I VECTOR VACCINE- 0.1 X 10⁸ PFU | 503 ± 88 (n=7) | 56 % |
| GROUP II VECTOR VACCINE- 1 X 10⁸ PFU | 380 ± 85 (n=8) | 69 % |
| GROUP III ANTI-PD-1 ANTIBODY (20μg/ANIMAL) | 513 ± 44 (n=9) | 56 % |
| GROUP IV ANTI-PD-1 ANTIBODY (100μg/ANIMAL) | 388 ± 80 (n=8) | 68 % |
|  |  |  |
| GROUP VI CONTROL (NO TREATMENT) | 1049 (n=1) |  |

FIG. 2

| GROUP | TUMOR VOLUME (mm³) DAY 55 MEAN ±SEM | %T/C DAY 55 |
|---|---|---|
| E#1-GROUP I- VECTOR VACCINE- 0.1 X 10⁸ PFU | 486 ± 86 (n=7/10) | 48% |
| E#1- GROUP II- VECTOR VACCINE- 1 X 10⁸ PFU | 371 ± 81 (n=8/10) | 36% |
| E#1- GROUP III- ANTI-PD-1 ANTIBODY (20μg/ANIMAL) | 487 ± 43 (n=9/10) | 48% |
| E#1- GROUP IV- ANTI-PD-1 ANTIBODY (100μg/ANIMAL) | 374 ± 73 (n=8/10) | 37% |
| E#1- GROUP VI- CONTROL (NO TREATMENT) | 1019 ± 18 (n=3/10) | - |
| E#2- GROUP A- VECTOR VACCINE +ANTI-PD-1 (1 X 10⁸ PFU + 100μg/ANIMAL) | 172 ± 30 (n=5/5) | 20% |
| E#2-GROUP B- VECTOR VACCINE+ANTI-PD-1 (0.1 X 10⁸ PFU + 20μg/ANIMAL) | 248 ± 39 (n=5/5) | 30% |
| E#2- GROUP C -CONTROL (NO TREATMENT) | 842 ± 36 (n=4/5) | - |

FIG. 4

| GROUP | TUMOR VOLUME (mm$^3$) DAY 55 MEAN ± SEM | %T/C DAY 55 |
|---|---|---|
| E#1- GROUP II- VECTOR VACCINE- 1 x 10$^8$ PFU | 371 ± 81 (n=8/10) | 36 % |
| E#1- GROUP IV-ANTI-PD-1 ANTIBODY (100μg/ANIMAL) | 374 ± 73 (n=8/10) | 37 % |
| E#1- GROUP VI- CONTROL (NO TREATMENT) | 1019 ± 18 (n=3/10) | - |
| E#2- GROUP A- VECTOR VACCINE +ANTI-PD-1 (1 x 10$^8$ PFU + 100μg/ANIMAL) | 172 ± 30 (n=5/5) | 20 % |
| E#2- GROUP C- CONTROL (NO TREATMENT) | 842 ± 36 (n=4/5) | - |

FIG. 6

| GROUP | TUMOR VOLUME (mm$^3$) DAY 55 MEAN ±SEM | %T/C DAY 55 |
|---|---|---|
| E#-1-GROUP I- VECTOR VACCINE- 0.1 X 10$^8$ PFU | 486 ± 86 (n=7/10) | 48% |
| E#1- GROUP III- ANTI-PD-1 ANTIBODY (20μg/ANIMAL) | 487 ± 43 (n=9/10) | 48% |
| E#1- GROUP VI- CONTROL (NO TREATMENT) | 1019 ± 18 (n=3/10) | - |
| E#2-GROUP B- VECTOR VACCINE+ANTI-PD-1 (0.1 X 10$^8$ PFU + 20μg/ANIMAL) | 248 ± 39 (n=5/5) | 30% |
| E#2- GROUP C -CONTROL (NO TREATMENT) | 842 ± 36 (n=4/5) | - |

FIG. 8

| TEST COMPOUND | MEDIAN SURVIVAL BY KM ANALYSIS |
|---|---|
| GROUP I<br>VECTOR VACCINE (0.1×10$^8$ PFU) | 60.5 |
| GROUP II<br>VECTOR VACCINE (1×10$^8$ PFU) | 71.5 |
| GROUP III<br>ANTI-PD-1 ANTIBODY (20 μg) | 64 |
| GROUP IV<br>ANTI-PD-1 ANTIBODY (100 μg) | 75 |
| GROUP VI<br>CONTROL (NO TREATMENT) | 56 |

FIG. 11

| TEST COMPOUND | MEDIAN SURVIVAL BY KM ANALYSIS |
|---|---|
| GROUP A<br>VECTOR VACCINE (1×10⁸ PFU) +<br>ANTI-PD-1 ANTIBODY(100 μg/ANIMAL) | 99.5 |
| GROUP B<br>VECTOR VACCINE (0.1×10⁸ PFU) +<br>ANTI-PD-1 ANTIBODY(20 μg/ANIMAL) | 79 |
| GROUP C<br>CONTROL (NO TREATMENT) | 62.5 |

FIG. 11A

| GROUP | CD8 (%POSITIVE CELLS) | CD11b (%POSITIVE CELLS) |
|---|---|---|
| VECTOR VACCINE (1×10$^8$ PFU)+ ANTI PD-1 ANTIBODY(100 μg/ANIMAL) | 2.1 | 6.2 |
| VECTOR VACCINE (0.1×10$^8$ PFU)+ ANTI PD-1 ANTIBODY(20 μg/ANIMAL) | 1.6 | 7.3 |
| CONTROL (NO TREATMENT) | 0 | 12.0 |

FIG. 14

COMBINATION CANCER THERAPY

CROSS-REFERENCE TO RELATED APPLICATIONS

This application claims priority and benefit under 35 USC 119(e) to U.S. Provisional Application Nos. 62/553,363 filed Sep. 1, 2017; 62/562,636 filed Sep. 25, 2017; and, 62/595,106 filed Dec. 6, 2017, the disclosures of which are all hereby incorporated herein by reference in their entireties.

FIELD OF THE INVENTION

The present invention relates to enhancing the body's own immune system to enable the body to amplify an immune response against cancer cells, by employing a combination therapy for cancer composed of an anti-checkpoint inhibitory antibody combined with a TAA/ecdCD40L therapeutic vaccine, for administration to an individual patient with cancer. The additive effect of Applicants' vaccine when combined with anti-checkpoint inhibitory antibody therapy, provides a more effective therapeutic approach, for eliminating cancerous tumors than either the vaccine or the anti-checkpoint inhibitory antibody therapy, when used as monotherapy.

BACKGROUND OF THE INVENTION

Applicants' experiment described herein is designed to, (i) in a first experiment (Experiment 1) compare by separate administration to different subjects over multiple times, the effect of monotherapy subcutaneous injection of the Ad-sig-hMUC-1/ecdCD40L vaccine vector therapy, with the monotherapy intraperitoneal injection of the anti-PD-1 checkpoint inhibitory antibody therapy, that is currently commercially available in the market, and then (ii) in a second experiment (Experiment 2) to test if administration over multiple times of the combination of the two therapies (vaccine vector therapy and a checkpoint inhibitor PD-1 antibody therapy), would provide for greater suppression of the growth rate of the mouse breast cancer E3 cell line which is positive for the human MUC-1 antigen, than either of the two therapies applied alone. Among other criteria, Applicants' goal was to determine if the administration of a TAA/ecdCD40L vaccine in combination with a PD-1 antibody, increases the number of antigen specific T cells that traffic into the tumor nodule(s) causing (i) an increase in efficacy by the number of tumor cell deaths, with reduced destruction of normal tissue (non-cancerous tumors) in an individual, (ii) an increase in the survival period of an individual, and (iii) allowing for a reduced dose level of antibody over a relatively shorter time period.

The current use of anti-PD-1 checkpoint inhibitory antibody therapy to release the T cell from the interaction of the PD-L1 ligand on tumor cells with the PD-1 receptor on T cells, which suppresses the response of CD8 effector T cells to tumor cells, is well known. Applicants' vaccine platform currently uses the immune-stimulatory protein CD40L in a tumor antigen specific manner, to activate dendritic cells, which in turn activate the body's CD8+ T cells and CD4+ T cells, to attack other cells that bear the targeted antigen.

In the current experimental study, anticancer activity of the Ad-sig-hMUC-1/ecdCD40L vaccine vector therapy (alone and in combination with an anti-PD-1 checkpoint inhibitory antibody therapy), was evaluated in immunocompetent BALB/c mice bearing syngeneic E3 mouse breast cancer cell line which is positive for the human MUC-1 gene. The E3 murine breast cancer cell line has been used as a syngeneic tumor model to test the efficacy of immunotherapy related products. The study was conducted for a period of approximately 16-18 weeks with regular observation of tumor volume, survival and body weight. Although, in this particular experiment, an adenoviral expression vector was used as the vaccine, there are several alternative versions of the vaccine as will be discussed.

Applicants' vaccine vector comprises a transcription unit encoding a secretable polypeptide, the polypeptide comprising a secretory signal sequence upstream of a tumor antigen upstream of the extracellular domain (ecd) of the CD40 ligand, which is missing or substantially all of the transmembrane domain rendering CD40L secretable. Also, provided are methods of generating an immune response against cells expressing a tumor antigen by administering an effective amount of the vaccine vector.

Definitions

"TAA" means target associated antigen and/or tumor associated antigen. The TAA would be the antigen of interest. It could, for example, be a mucin antigen, "Cancer" or "Tumor" means any type of cancer and cancer metastasis be it a solid or non-solid cancer type, whether carcinoma, sarcoma, melanoma, lymphoma, leukemia.

"Ad" means an adenoviral vector, however any viral or non-viral expression vector any be employed that when administered in vivo can enter target cells and express an encoded protein. See below "vector" definition.

"ecd" means the extracellular domain of a CD40 ligand and specifically excludes at least the transmembrane domain that inhibits secretion.

"MUC-1" refers to one type of a mucin antigen although any other of the forms of a mucin antigen may be used "sig" means secretory signal "AB" means antibody "µg" means micrograms "mg" means milligrams "mm" means millimeters "sc" means subcutaneous "VPU" means viral particles per unit "DCs" means dendritic cells "baseline" means the tumor volume (TV) at day 1 for Experiments 1 and 2. See Randomization & study initiation in Tables 1 and 2 and FIG. 15 for TV selection between 50-100 $mm^3$ for study initiation at day one.

"effective amount" means an amount of a cancer agent administration and/or treatment according to the teachings of the present invention that is effective to generate (or contribute to the generation) an immune response in the recipient in treating cancer as described herein. The "effective amount" or dose level will depend upon a variety of factors and may vary according to the disorder being treated, the activity of the specific compound, the route of administration, the rate of clearance of the viral vectors, the drugs used in combination or coincident with the viral vectors, the severity of the disorder, the clinical history of the patient, the patient's age, body weight, sex, diet, physical condition, and/or general health, duration of treatment, and so forth. The effective amount could be more or less than the specified amounts used in the experiment and depend upon the considerations taken into account to determine the therapeutically effective amount. Various general considerations taken into account in determining the therapeutically effective amount are known to those of skill in the art and are described, e.g. in Gilman et al, eds., Goodman and Gilman's "The Pharmacological Bases of Therapeutics, Pergamon Press; and Remmington's Pharmaceutical Sciences, Mack Publishing Co., Easton, PA.

"combination therapy", "combined treatment" or "in combination" means at least a vaccine and checkpoint inhibitor treatment, at the same time and/or at different times, within a prescribed time period, with at least the said two distinct therapeutic agents.

"checkpoint inhibitor" and/or "antibody" means any one or more of commercial drugs and/or non-commercial drugs designed, whether or not commercialized and/or sold to administer to an individual (or an animal), for unblocking checkpoints in the body which may prevent the immune system, in part or in whole, from attacking a cancer using the body's T cells, and regardless of how administered.

"PD-1" means one example of a checkpoint inhibitor antibody

"cell line", means in the example experiment of this particular application, a hMUC-1 positive E3 mouse breast cancer cell line in BALB/c mice (Victoria Carr-Brendel et al, Cancer Research 60: 2435, 2000; EL-Nasir Lalani et al, JBC 266: 15420, 1991).

"PFU" means the number of particles capable of forming plaques per unit volume

"TGI" means Tumor Growth Inhibition

"MHC" means major histocompatibility complex

"SEM" means structural equation modeling

"Kaplan-Meier" or "K-M" means the Kaplan-Meier estimator, also known as the product limit estimator, is a non-parametric statistic used to estimate the survival function from lifetime data. In medical research, it is often used to measure the fraction of patients living for a certain amount of time after treatment. The estimator is named after Edward L. Kaplan and Paul Meier, who each submitted similar manuscripts to the Journal of the American Statistical Association.

"MDSC" means myeloid-derived suppressor cell.

"CD11b" is a marker for myeloid inhibitory cells.

"ORR" means overall response rate.

"TAA" means tumor/target associated antigen.

"Secretion", is used in reference to the fusion protein TAA/ecdCD40L, and means that the fusion protein includes elements (such as the secretory or signal sequence) that cause secretion of the TAA/ecdCD40L fusion protein to occur, as opposed to an element such as a transmembrane domain of a cell that does not allow secretion to occur.

"Antigen" means broadly any antigen or portion thereof to which a human, mammal, bird or other animal can generate an immune response. Antigen, as used herein refers broadly to a molecule that contains at least one antigenic determinant to which the immune response may be directed. The immune response may be cell-mediated, humoral or both.

"Vector" is a term that contains a transcription unit (aka the "expression vector") and as used herein refers to a viral and/or non-viral expression vector that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like.

Viral vectors are preferably made replication defective in normal cells. For example, see U.S. Pat. Nos. 6,669,942; 6,566,128; 6,794,188; 6,110,744 and 5,133,029. The vector can be administered parenterally, such as intravenously, intra-arterially, intramuscularly, subcutaneously, or the like. Administration can also be orally, nasally, rectally, trans-dermally or aerosol inhalation. The vectors may be administered as a bolus or slowly infused. The vector in the instant application is preferably administered subcutaneously.

"Transcription unit" as it is used herein is in connection with an expression vector, means a stretch of DNA that is transcribed as a single, continuous mRNA strand by RNA polymerase, and includes the signals for initiation and termination of transcription. The transcription unit is in operable linkage with transcriptional and/or translational expression control elements such as a promotor and optionally any upstream or downstream enhancer element(s). A useful promoter/enhancer is the cytomegalovirus (CMV) immediate-early promoter/enhancer. See U.S. Pat. Nos. 5,849,522 and 6,218,140.

"CD40 ligand" (CD40L), as used herein refers to a full length or portion of the molecule known as CD154 or TNF5. CD40L is a type II membrane polypeptide having a cytoplasmic domain at its N-terminus, a transmembrane region and then an extracellular domain ("ecd") at its C-terminus. Unless otherwise indicate the full length CD40L is designated herein as CD40L. The nucleotide and amino acid sequence of CD40L from mouse and human is well known in the art. Also included within the meaning of CD40L are variations in the sequence including, but not limited to, conservative amino acid changes and the like which do not alter the ability of the ligand to elicit an immune response in conjunction with the fusion protein.

TAA/ecdCD40L Vaccine Platform

The TAA/ecdCD40L targeted vaccine platform is fully described in several patents and publications by at least one of the Applicants. The CD40L is an immuno-stimulatory protein. A modified form of the CD40L protein, the extracellular domain (the ecd), is attached to the TAA to the CD40 receptor on dendritic cells (DCs) to activate the dendritic cells and promotes (using a selected mucin fragment) the presentation of the human MUC-1 antigen on Class I as well as Class II MEW and in turn activates T cells which attack and kill the human MUC-1 positive cancer cells. See, for example, U.S. Pat. Nos. 8,119,117, 8,299,229, and/or 9,533,036. The TAA (target associated antigen and/or tumor associated antigen), is the targeted antigen of interest for a particular class of patients with cancer. In U.S. Pat. No. 8,299,229, the TAA was a fragment of the human mucin antigen and in particular the human MUC-1 was the antigen of interest. So, the TAA/ecdCD40L is a targeted vaccine targeting the tumor of interest (antigen specific) in contrast to the anti-PD-1 checkpoint inhibitory antibody which although binds to the PD-1 receptor on T cells, is not targeted to any particular tumor associated antigen (antigen non-specific).

There are several versions of this vaccine that may be applied for use in the instant invention: (a) one in which the TAA/ecdCD40L transcription unit is embedded in a replication incompetent adenoviral vector (Ad-sig-TAA/ecdCD40L) which is used as an initial priming injection, followed by at least two sub-cutaneous injections of the TAA/ecdCD40L protein; (b) one in which the vaccine consists solely of the TAA/ecdCD40L protein, and (c) one in which the transcription unit for the TAA/ecdCD40L protein is inserted into a plasmid DNA expression vector. The TAA is connected through the linker to the aminoterminal end of the extracellular domain of the potent immunostimulatory signal CD40 ligand (CD40L). The preferred TAA/ecdCD40L protein used in the instant experiment includes a mucin antigen fragment and is an adenoviral expression vector Ad-sig-hMUC-1/ecdCD40L. Construction of the adenoviral expression vector Ad-sig-hMUC-1/ecdCD40L that is employed in the instant application, may be gleaned or derived from U.S. Pat. No. 8,299,229 in which one of the instant applicants is listed as a co-inventor. See columns 13-16, of said '229 patent, in which construction of said adenoviral expression vector is addressed in significant detail. Also, see discussion and description of expression vectors and adenoviral expression vectors, throughout the patent specification and drawings.

The attachment of the TAA to the CD40L accomplishes two things: (a) the binding of the TAA/ecdCD40L protein to the CD40 receptor on the dendritic cells (DCs) as well as on the B cells and T cells, activates these cells thereby replacing the CD40L signal which is missing on the plasma membrane of the CD4 helper T cells of older individuals; and (b) once the TAA/ecdCD40L protein is engaged on the CD40 receptor of the DC, the entire TAA/ecdCD40L protein is internalized into the dendritic cells (DCs) in a way that allows the TAA to be processed through the Class I as well as the Class II MHC presentation pathways. The activated TAA loaded DCs then migrate to the regional lymph nodes (8) where they can activate and induce expansion of the TAA specific CD8 effector T cells.

These antigen specific CD8 effector cells become increased in number in the lymph nodes, egress from the lymph nodes into the peripheral blood. The antigen specific CD8 effector T cells exit the intravascular compartment and enter into the extravascular sites of inflammation or infection. In addition to showing that this vaccine increases the antigen specific CD8 effector T cells in the sites of inflammation, it has been shown that the activation and expansion of the B cells by the TAA/ecdCD40L protein increases the levels of the TAA specific antibodies in the serum.

As noted in U.S. Pat. No. 9,533,036, Applicants' vaccine provides for increasing the immune responsiveness of an individual having CD4 T cells exhibiting reduced levels of CD40 ligand (in cases which include not only older individuals but younger individuals having reduced levels of CD40 ligand), as compared to young, healthy individuals to vaccination against a cancer antigen or an infectious agent antigen. This is accomplished by administering to the individual an effective amount of an expression vector having a transcription unit encoding a secretable fusion protein, having a cancer or infectious agent antigen and ecdCD40 ligand, where there is an initial administration of the expression vector vaccine followed by multiple subsequent boosts of the vaccine. As also stated, the vaccine therapy provides for a long-term memory of at least one year.

Although not wishing to be bound by any theory, it is believed that the cells infected in the vicinity of the subcutaneous injection of the vector release the mucin antigen/CD40 ligand fusion protein which then binds to the CD40 receptor on antigen presenting cells which bound fusion protein is then taken up by antigen presenting cells e.g. dendritic cells in the vicinity of the Ad-sig-hMUC-1/ecdCD40L vaccine expression vector infected cells. The internalized human mucin antigen would then be digested in the proteasome with the resultant mucin antigen peptides trafficking to the endoplasmic reticulum where they would bind to Class I MHC molecules. Eventually the dendritic cells would present the human mucin antigen bound to the Class I MHC molecule on the surface of the dendritic cells. Activated, tumor antigen-loaded antigen presenting cells (DCs) would then migrate to lymphocyte bearing secondary lymphoid organs such as the regional lymph nodes or the spleen which are in the lymphoid drainage area of the original injection site of the vaccine expression vector.

During the two weeks of continuous release of the human mucin antigen/ecdCD40L protein, CD8 cytotoxic T cell lymphocytes competent to recognize and kill cells which carried the tumor associated antigens would be expanded in the lymph nodes and spleen by the presence of activated and antigen-loaded dendritic cells. The continuous nature of the stimulation and expansion of the mucin antigen specific cytotoxic T cells by the continuous release from the vector infected cells is believed to generate an immune response which would be greater in magnitude than is possible using a vector which carried a transcription unit encoding a fusion protein composed of the human mucin antigen linked to the unmodified CD40 ligand which is non-secretory. In the example used in the experiment, the TAA is a human mucin antigen peptide from human MUC-1, although other peptides and other antigens could be used. For example, in U.S. Pat. No. 8,119,117, there is shown the use a the E6 or E7 protein of HPV. In U.S. Pat. No. 8,299,229, at column 8 is shown a Table 1 with mucin peptides that could be used as the TAA.

In preferred embodiments, the immune-therapeutic expression vector may be a viral expression vector or a non-viral expression vector; e.g. an adenoviral expression vector; the antigen fragment is from a mucin selected from the group comprising a MUC1, MUC2, MUC3, MUC3A, MUC3B, MUC4, MUC5AC, MUC5B, MUC6, MUC7, MUC8, MUC9, MUC12, MUC13, MUC15, MUC16, MUC17, and MUC19-MUC22; the mucin antigen includes a fragment from the extracellular domain of a mucin; or at least one tandem repeat of a mucin; the mucin antigen fragment used in the instant invention is from MUC1; and the transcription unit includes a sequence that encodes a linker between the tumor antigen and the CD40 ligand. Suitable linkers may vary in length and in composition. The expression vector may include a human cytomegalovirus promoter/enhancer for controlling transcription of the transcription unit. The tumor cells may be other than of the mucin family, may be cancer cells of any kind or character, and the method results among other things in the generation of cytotoxic $CD8^+$ T cells against the cancer cell or mucin. The cancer can be any cell in a subject undergoing unregulated growth, invasion or metastasis. The cancer can be a myeloid leukemia, bladder cancer, brain cancer, breast cancer, prostate cancer, ovarian cancer, nervous system cancer, head and neck cancer, squamous cell carcinoma of head and neck, kidney cancer, lung cancer, such as small lung cancer and non-small cell lung cancer (NSCLC), pancreatic cancer, colon cancer, and so forth.

Checkpoint Inhibitors

An important capability of the immune response system is its ability to distinguish between normal cells in the body and those it sees as "foreign" such as cancer cells. This capability enables the immune system to attack the cancer (foreign) cells while leaving the normal cells undamaged. One such mechanism used by the immune response is the class of immunologic "checkpoints"—molecules such as the PD-1 receptor which is present on CD8 effector T cell lymphocytes cells. When the PD-1 ligand expressed on normal cells of the body, or in the case of patients with cancer, the PD-L1 on the tumor cells binds to the PD-1 receptor on T cells, those T cells are suppressed and eventually die. This is a mechanism through which tumor normal cells of the body are protected from attach by the immune response. This is also a mechanism through which cancer cells can escape attack by the immune response. Administration of an anti-PD-1 or PD-L1 inhibitory antibody (including but not limited to an initial administration of the antibody with multiple subsequent boosts of the antibody) which blocks the interaction of the PD-1 receptor on T cells and the PD-L1 ligand on cancer cells, results in the suppression of the growth of the PD-L1 positive tumor cells. CTLA-4 is another protein on some T cells that acts as a type of "off switch" to keep the immune system in check.

PD-1 is a checkpoint protein on immune cells called T cells. There are several different types of check point of inhibitory receptors on activated T cells. PD-1 is just one example. It normally acts as a type of "off switch" that helps keep the T cells from attacking the normal cells in the body. But when the PD-1 receptor on effector T cells attaches to PD-L1 on a tumor cell, that cell is protected. When PD-1 binds to PD-L1, it basically tells the T cells to leave the cell bearing the PD-L1 alone. Some cancer cells have large amounts of PD-L1, which helps them evade immune attack. Monoclonal antibodies that target either PD-1 or PD-L1 can block this binding thereby boosting the immune response against cancer cells. These antibodies have shown a great deal of promise in treating certain cancers. Current prevailing practice is to administer checkpoint inhibitor therapy every two to three weeks generally though intra-venous infusion (although other methods of drug delivery may be used such as, for example, through the use of nano-technologies), over a two-year period, to achieve efficacy.

Drug delivery is typically concerned with both quantity and duration of drug presence. It may involve medical devices or drug-device combination products. Drug delivery technologies modify drug release profile, absorption, distribution and elimination for the benefit of improving product efficacy and safety, as well as patient convenience and compliance. Most common routes of administration include the preferred non-invasive peroral (through the mouth), topical (skin), transmucosal (e.g. rectal), and inhalation routes. Many medications are susceptible to enzymatic degradation or cannot be absorbed into the systemic circulation efficiently due to molecular size and charge issues to be therapeutically effective. For this reason, many protein and peptide drugs have to be delivered by injection or a nanoneedle array. In any event, it is believed that any appropriate drug delivery mechanism for a checkpoint inhibitor can be other than infusion and can be other than the use of subcutaneous administration approach for Applicants vaccine. Unfortunately, checkpoint inhibitor antibody therapy, although a considerable advance in the treatment of some cancers, does not target tumor specific antigens. Moreover, a large subset of cancer patients fails to respond to these new immunotherapies and this has led to an intensified research on combination therapies to overcome these and other issues. There are currently many studies in effect to determine how to best increase the efficacy of checkpoint inhibitors by combining checkpoint inhibitor therapy with a multitude of other possible therapy solutions. Some feel that combining checkpoint inhibitor therapy with radiation therapy is one solution. Others are combining checkpoint inhibitor therapy with chemotherapies. Yet others are exploring combinations with chemoradiotherapies. Still others are studying the use of several novel molecules. Most experts do not envision immunotherapy as a substitute for traditional therapies like surgery, radiation and chemotherapy. Also, it is known that checkpoint inhibitor dosing and scheduling are cost drivers. Applicants believe that by combining the administration of a non-targeted PD-1 checkpoint inhibitory antibody receptor with a TAA/ecdCD40L vaccine that targets a specific tumor antigen (e.g. MUC-1), it would be possible that such a combination will increase the magnitude of the anti-tumor immune response and, at the same time, might reduce the dosing and/or dose scheduling which additionally might reduce any potential toxicity including any side effect(s) to the patient.

Applicants are of the view that tumors which are "cold" or non-inflamed (low level of infiltrating CD8 effector T cells), will respond to the combination of the TAA/ecdCD40L vaccine and anti PD-1 antibody therapy, if appropriately stimulated as with the TAA/ecdCD40L vaccine therapy, which is a targeted therapy that increases TAA specific CD8 T cells in $TAA^+$ subcutaneous (sc) tumor nodules in mice. See FIGS. 4 and 5B from page 5705 Tang Y C et al, Journal of immunology 177:5697-5707, 2006). Notwithstanding the foregoing, Applicants understood that these two different immunotherapy approaches are significantly distinct in both, their administration (subcutaneous and infusion or other delivery approach used), and their manner of operation. The checkpoint inhibitor is non-antigen specific with administration of an anti-PD-1 or PD-L1 inhibitory antibody to block the interaction of the PD-1 receptor on T cells and the PD-L1 ligand on cancer cells. In contrast, the TAA/ecdCD40L vaccine therapy is antigen specific and acts through dendritic cell activation. Clearly, drug development is not a predictable science. Use of the two distinct therapies in combination that work through entirely different mechanisms, may not be compatible, one with the other, for a variety of reasons. Accordingly, it was a goal of the experiment to evaluate the compatibility of these two distinct therapies and determine if their use in combination is compatible and, if so, might it result in any unacceptable or intolerable toxic side effects. For this reason, some maximize the odds of a patient responding to at least one drug, for example, by treating patients sequentially rather than simultaneously, thereby reducing compounding side effects, enabling higher dosages when effective, and potentially yielding lowering treatment costs. An additional goal of the experiment was to see if the addition or combination of TAA/ecdCD40L therapy to anti-PD-1 antibody therapy, might, in fact, not only possibly convert tumors from cold to hot but thereby increase overall response rates to PD-1 antibody therapy in addition to the therapeutic effect resulting from the vaccine therapy alone.

The experiment protocol called for injecting BALB/c mice sc with 1.5 million E3 mouse breast cancer cell line (positive for human MUC-1), and allowing the tumor to grow to 75-100 $mm^3$ (palpable) and treat separately with Ad-sig-hMUC-1/ecdCd40L vaccine and anti-PD-1 antibody, and then with a combination of the same and compare with no treatment control mice or E2 control no treatment mice, to help determine the answer(s) to one or more goals of the experiment.

The instant invention which involves the combined administration of an anti-PD-1 checkpoint inhibitory antibody therapy and TAA/ecdCD40L vaccine therapy over a common time period, after extensive experimentation, was found to increase the suppressive effect on the growth of tumor nodules in a mouse model so that the suppressive effect of the combination on the growth of TAA positive cancer cells was significantly greater than either the antibody or the vaccine when used alone as a monotherapy. Examples of checkpoint inhibitor antibodies which block the interaction of the PD-1 receptor on T cells with the PD-L1 or PD-L2 ligand on cancer cells include, for example, Pembrolizamab, Nivolumab, Atezolizumab, Avelumab, Tremelimumab, Ipilimumab and Durvalumab. Any one or more of the above example antibodies or similar antibodies, which release T cells from the suppressed effect of checkpoint inhibitors, thereby enabling T cells to attack tumor cells in the body, is hereby designated as a "checkpoint inhibitor".

Description of Experiment

Thus, this result depicts that the vaccine therapy, when combined with the PD-1 antibody therapy, promotes the entry of CD8 effector T cells into the cancerous tumor tissue, and thus it is believed to convert the cold non-inflamed cancerous tumor tissue to more highly responsive cancerous tumor tissue.

Materials & Test System
Species: *Mus musculus*
Strain: BALB/c
Source: Envigo
Sex & Age: Female; 5-6 weeks
Body weight: 20-22 g
No. of groups: 8
No. of animals/group: n=10
Cancer cell line: hMUC-1 positive E3 mouse mammary cancer cell line
Cell inoculation density: $1.5 \times 10^6$ cells/animal in 100 µl of serum free medium (containing 20% matrigel)
Site of cell injection: Mammary fat pad ($4^{th}$ pair)
Study initiation: Tumor volume (50-100 mm$^3$)
Duration of the study: 16-18 weeks
Test item: Ad-sig-hMUC-1/ecdCD40L Vaccine Vector; *Anti-PD-1 antibody
Storage Conditions: Ad-sig-hMUC-1/ecdCD40L: −60° C. (NOTE: These vials are stored in a Revco Freezer at −60° C. When a vial is thawed out, the vial is swirled in a water bath at 37° C. until the central core of ice is just barely detectable and then is removed from the water bath). Anti-PD-1 antibody: 2-8° C.
Dose & Dosing schedule: Ad-sig-hMUC-1/ecdCD40L Vaccine Vector—$0.1 \times 10^8$ PFU, $1 \times 10^8$ PFU, $10 \times 10^8$ PFU on Days 1, 8, 22, 40 and 60 Anti-PD-1 antibody—20 µg, 100 µg and 250 m/animal on Days 1, 4, 7, 10, 13, 17, 20, 23, 40 and 60
Route of dosing: Subcutaneous—Ad-sig-hMUC-1/ecdCD40L Vaccine Vector Intraperitoneal—Anti-PD-1 antibody
Tumor volume & Body weight measurement: Once every two days
Tumor end points Sixty days after injection of the tumor cells, or when size of tumor nodule greater than 1 cm (1000 mm$^3$) diameter
NOTE: Anti-PD-1 antibody was procured from BIOXCELL—VivoMAb anti-mouse PD-1 (CD279); Clone: RMP1-14 Catalog #: BE0146

The E3 Cell Line

The E3 cell line used in Applicants' experiment has been supplied for the purposes of this experiment, under license, from CRT (Cancer Research Technology, Limited). The materials known as E3 cell line, a human MUC-1 positive E3 mouse breast cancer cell line, details of which have been published in Victoria Carr-Brendel et al, Cancer Research 60: 2435, 2000; El-Nasir Lalani et al, Journal of Biological Chemistry 266: 15420, 1991

Study Details

The Study details for the experiment are laid out in Table I below:

| E3 Cell inoculation density | Tumor volume @ study initiation | No. of animals/group | Group | Treatment | Dose |
|---|---|---|---|---|---|
| $1.5 \times 10^6$ hMUC-1 positive E3 mouse mammary cancer cells/animal in 100 µl of serum free medium (containing 20% matrigel) - in mammary fat pad | 50-100 mm$^3$ | Experiment 1 - 10 | Group I & II - Vector Vaccine | Ad-sig-hMUC-1/ecdCD40L Vaccine Vector | $0.1 \times 10^8$ PFU |
| | | 10 | | Ad-sig-hMUC-1/ecdCD40L Vaccine Vector | $1.0 \times 10^8$ PFU |
| | | 10 | Group III & IV-Anti-PD-1 Antibody (InVivoMAb anti-mouse PD-1 (CD279); Clone: RMP1-14 Catalog#: BE0146; Source-BIOXCELL) | Anti-PD-1 antibody | 20 µg/animal |
| | | 10 | | Anti-PD-1 antibody | 100 µg/animal |
| | | 10 | Group V (No Treatment Control Mice) | — | — |

-continued

| | | | | Ad-sig-hMUC-1/ecdCD40L Anti-PD-1 antibody | Group A - 0.1 × 10⁸ PFU & 20 ug Group B - 1.0 × 10⁸ & 100 ug |
|---|---|---|---|---|---|
| | Experiment 2 - 5 animals for each Group | Group A & B Vector Vaccine and Anti-PD-1 Antibody Group C - Control (No treatment) | | | |

| E3 Cell inoculation density | Route of administration | Dosing schedule | Tumor volume & body weight measurement | Study termination & |
|---|---|---|---|---|
| 1.5 × 10⁶ hMUC-1 positive E3 mouse mammary cancer cells/ animal in 100 μl of serum free medium (containing 20% matrigel) - in mammary fat pad | Subcutaneous | Days 1, 8, 22, 40 and 60 | Once every two days | End points 60 days after injection of the tumor cells, or when size of tumor nodule greater than 1 cm (1000 mm³) in diameter End points: Survival (Day 100) Growth rate of subcutaneous tumor (tumor volume vs time), and Histopathological analysis of the subcutaneous tumors at the time of sacrifice IHC - mammary fat pad tumor - stained for CD8 effector T cells |
| | Subcutaneous | Days 1, 8, 22, 40 and 60 | | |
| | Intraperitoneal | Days 1, 4, 7, 10. 13. 17, 20, 23, 40 and 60 | | |
| | Intraperitoneal | Days 1, 4, 10. 13. 17, 20, 23, 40 and 60 | | |
| | Vaccine vector - Subcutaneous Anti-PD-1 antibody Intraperitoneal | Days 1, 8, 22, 40, and 60 Days 1, 4, 7, 10, 13, 17, 20, 23, 40, and 60 | Once every two days | |

NOTE:
In Experiment 1, the dose of vaccine expression vector (Ad-sig-hMUC-1/ecdCD40L) and the anti-PD-1 antibody (Groups I-IV) were given to separate test mice as monotherapy, as per the values stated above in Table I, and were shown to partially suppresses the growth rate of the hMUC-1 positive E3 mouse mammary cancer cell line, and on Day 40 the two above identified therapy combinations, Group A and Group B, were chosen for Experiment 2 for the combination therapy experiment.

Dosing Schedules: Although a preferred dosing schedule therapy combination (of vaccine and antibody) is disclosed in Table 1 above and Table 2 below, and FIG. 15, for both the low dose and high dose therapy combinations, alternative dosing administrations over different periods of time, might be used for a breast cancer cell line, and/or for different kinds of cancer that may be alternatively determined for best overall response and overall survival, measured per immune-related response criteria. Preferred administration amounts as well as timing between administrations, might also be preferably those that were determined separately, in separate clinical uses of the vaccine and antibody. For example, in some instances, antibody administration dosing amounts may also vary by the number of milligrams per kilogram weight of a patient, whereby the administrations are every two or three weeks.

Preparation of Tumor Cells—Experiment 1

All cell culture procedures in the instant experiment, have been performed in laminar flow hood following sterile techniques. The E3 cell line was grown up in medium supplemented with 10% fetal bovine serum (FBS) using T75 and T150 mm culture flasks.

The vaccine or anti-PD-1 antibody is administered as noted below either at dose levels which are at the known therapeutic levels in the mouse (100 million VP of the vaccine and 100 micrograms of the anti-PD-1 antibody) and in other instances the doses were below the therapeutic level in the mouse (10 million VP of the vaccine and 20 micrograms of the anti-PD-1 antibody). The animal dose levels also could be as much as 250 μg which is a known therapeutic level for the mouse.

Human dose levels which are comparable to those shown in the chart below, would normally be in the range of $0.1 \times 10^{11}$ VPU to $1.0 \times 10^{11}$ vector particles (VP), whereas comparable human antibody dose levels of anti-PD-1 antibody might normally be in the range of 20 mg to 250 mg. Administration of dose levels of some antibodies (whether PD-1, PD-L1 and/or CTLA4, are based upon human weight. For example, human dose levels for some antibodies might generally be anywhere from 2 mg/kg to 12 mg/kg.

With administration of any therapy and/or drug, careful consideration needs to be given to the possibility of toxicity, and, accordingly, it is important to carefully evaluate several dose levels of any treatment to be provided. With this in mind, dose levels chosen for the instant experiment leaned toward minimizing rather than maximizing the experimental dose levels understanding that these might be used as a guide in terms of applying the combined therapy for humans. Accordingly, in the experiment Applicants choose to use a lower equivalent vaccine dose level that Applicants have been using in a clinical trial for humans where no toxicity issue was encountered, and a lower equivalent dose level of an antibody that is believed to have less of a toxic effect that is used for human application.

Toxicity of the Anti-PD-1 Antibodies: The toxicities of the anti-PD-1 antibodies has been reviewed (J. Naidoo, D B Page and B T Li et al., Toxicities of the anti-PD-1 and anti-PD-1 immune checkpoint antibodies. Annals of Oncology 26:2375-2391, 2015.) These side effects include inflammatory states of the skin, liver, lung, gastrointestinal tract as well as the endocrine glands, which resemble mild autoimmune diseases. Accordingly, it would be preferred, if effective, to use the lowest possible dose levels of the anti-PD-1 antibodies for treatment.

Applicants believed that by selectively combining their TAA/ecdCD40L vaccine with a checkpoint inhibitory antibody in Experiment 2, that there was the possibility that some of these toxicity issues associated with the Anti-PD-1 antibody may be reduced because the anti-PD-1 antibody might be effective at much lower doses when given in combination with the TAA/ecdCD40L vaccine, and/or fewer doses of the anti-PD-1 antibody may be needed.

TABLE 2

Therapeutic Administration and Related Considerations

| Test compound | Route | Dose | Dose volume | Schedule |
|---|---|---|---|---|
| Ad-sig-hMUC-1/ecdCD40L Vaccine Vector | Subcutaneous on the back | $0.1 \times 10^8$ PFU | 100 μl/animal | Days 1, 8, 22, 40 and 60 |
| | | $1 \times 10^8$ PFU | 200 μl/animal | |
| Anti-PD-1 antibody | Intraperitoneal | 20 μg/animal | 100 μl/animal | Days 1, 4, 7, 10. 13. 17, 20, 23, 40 and 60 |
| | | 100 μg/animal | 100 μl/animal | |

Observations and End Points (as Related to Table 2 and FIG. 15)

Body weight and volumes of the tumors were measured once every two days during the study period.

Tumor volume was calculated using the following formula:

Tumor Volume (mm³)=$V=Pi/6(LD)(PD)2$ where LD=longest diameter and PD=the diameter perpendicular to the LD The % tumor growth inhibition (TGI) was calculated and compared statistically with vehicle control.

Survival data is also listed and depicted.

Necropsy: Collection of tumor: At the end of the experiment period (Day 100), all animals that were alive were euthanized and tumor nodule from mammary fat pad will be harvested.

Histology: The tumor tissue was fixed in 10% neutral buffered formalin for 24 hours. Then the tumor tissue was subjected to processing and paraffin embedded tissue blocks were prepared. Fine sections of five-micron thickness was taken and stained with hematoxylin and eosin. The pathologist screened the slides for the morphological and inflammatory changes in the tumor, pleomorphism, fibrovascular stroma, mitotic figures, area of necrosis etc.

IHC: Unstained Poly-1-lysine slides were used for IHC detection of mouse CD8 effector T cells.

FIGURES

FIG. 1 graphically depicts in Experiment 1, tumor volume (mm³) growth for each of the respective five groups (four monotherapy groups and control) versus days (from day 1 to day 57, whereby at day 55 all control mice had expired).

FIG. 1A graphically depicts in Experiment 1, tumor volume (mm³) growth for each of the respective five groups (four monotherapy groups and one control) versus days up to day 99 when Experiment 1 was terminated.

FIG. 2 is a Table listing of the graphical representation in FIG. 1 for the tumor volume for the respective monotherapy groups in FIG. 1 at day 57 of the first experiment portion, and the TGI (tumor growth inhibition), at the last day of control group animal life at day 55.

FIG. 4 is a tabular listing of the graphical representation in FIG. 3, where the tumor volume column stated is at day 55 of Experiment 2, and the % T/C (tumor volume over control volume) represents the tumor growth percentage at day 55.

Figure 5:
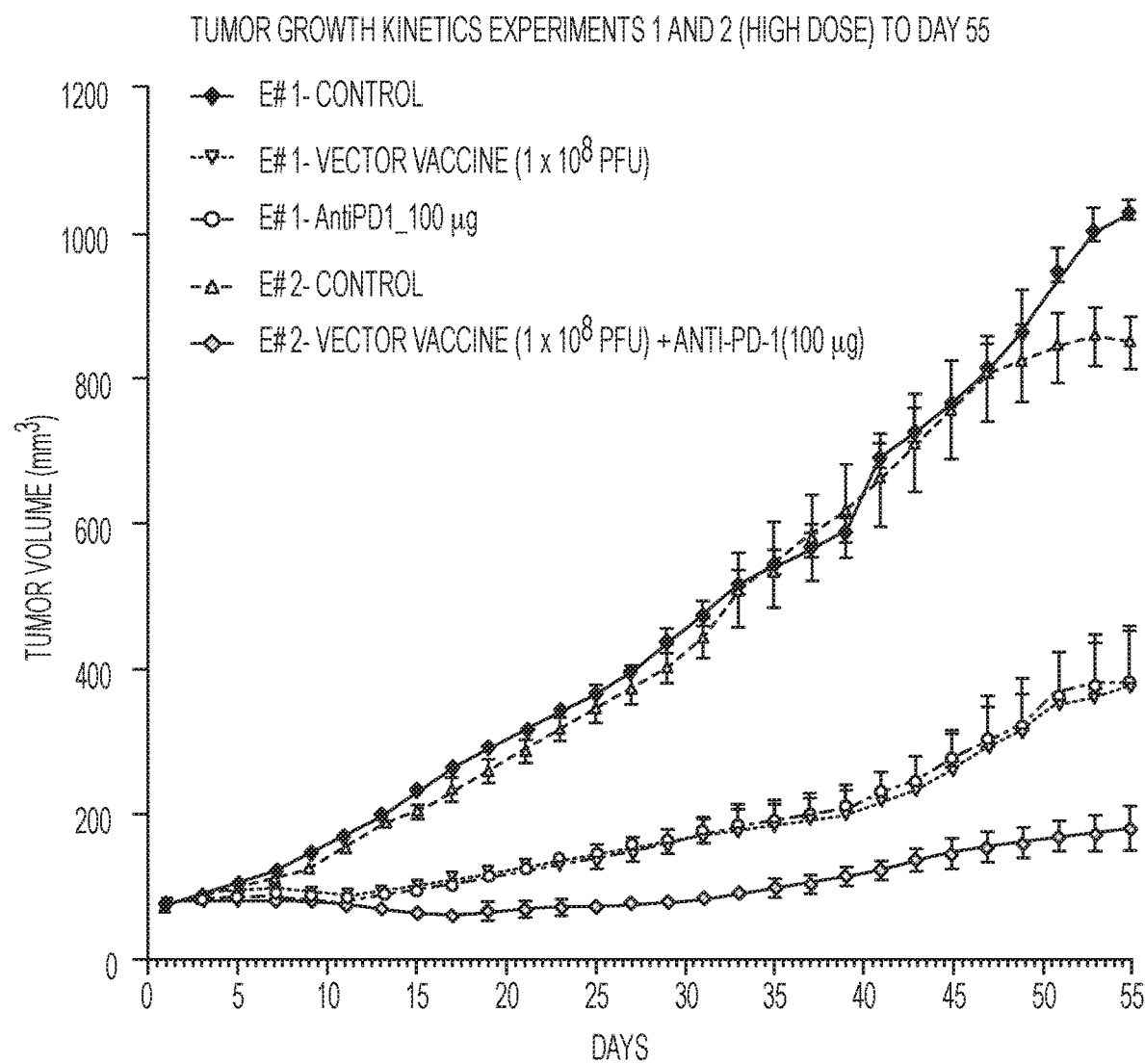

FIG. 5 graphically depicts the tumor growth kinetics versus days of solely the two monotherapy high dose groups of Experiment 1 and the combination high dose of Experiment 2, along with both controls, up to the last day 55 of control animal life.

Figure 5A:
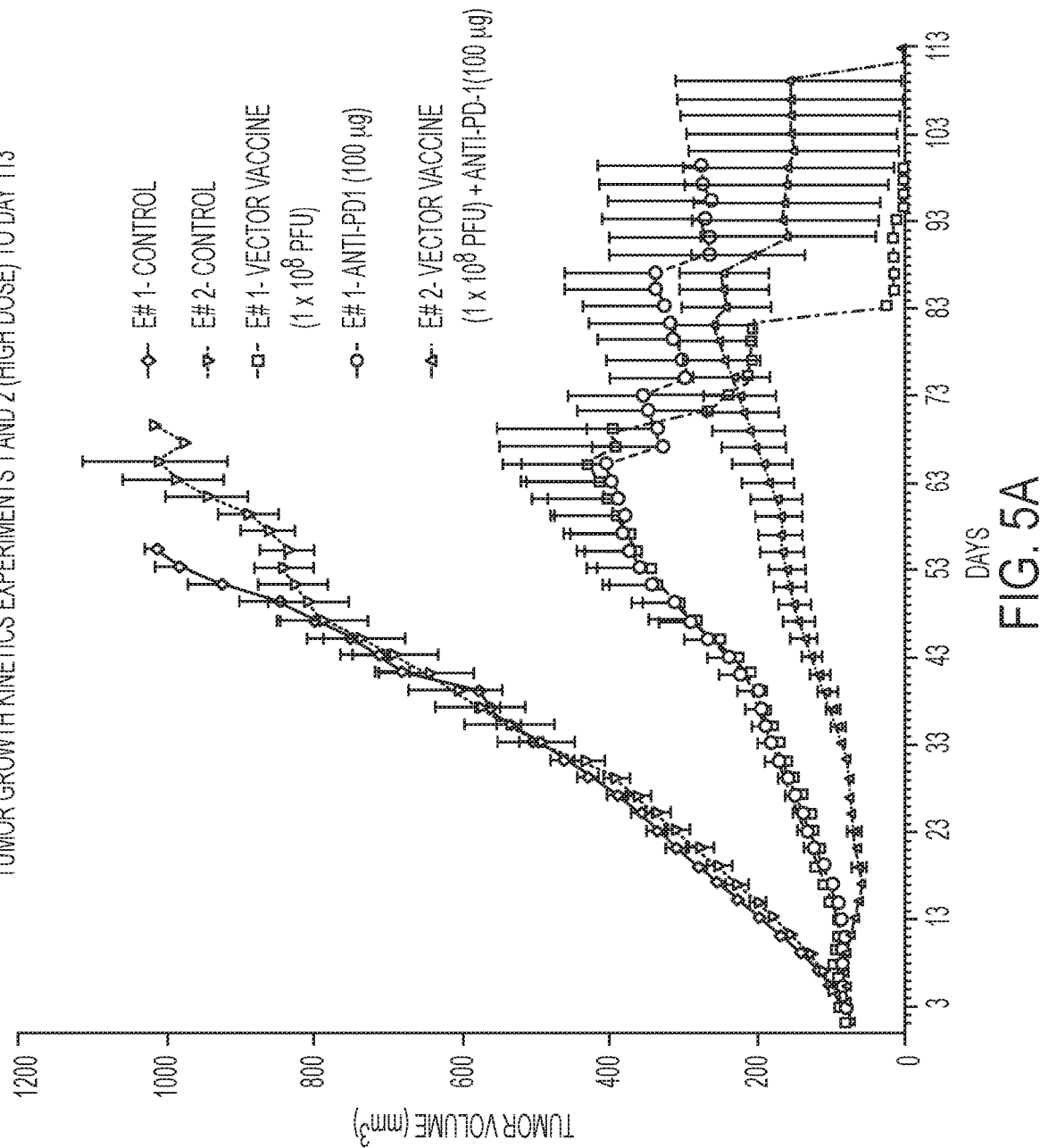

FIG. 5A graphically depicts the tumor growth kinetics of the high dose combination (of Experiment 2), and its respective high dose monotherapies (of Experiment 1), with both controls, up to the termination of Experiment 1 at 99 days and Experiment 2 at day 113.

FIG. 6 is a tabular listing of values of the graphic representation in FIG. 5 of solely the high dose groups and the controls of Experiments 1 and 2, and % T/C at day 55.

Figure 7:
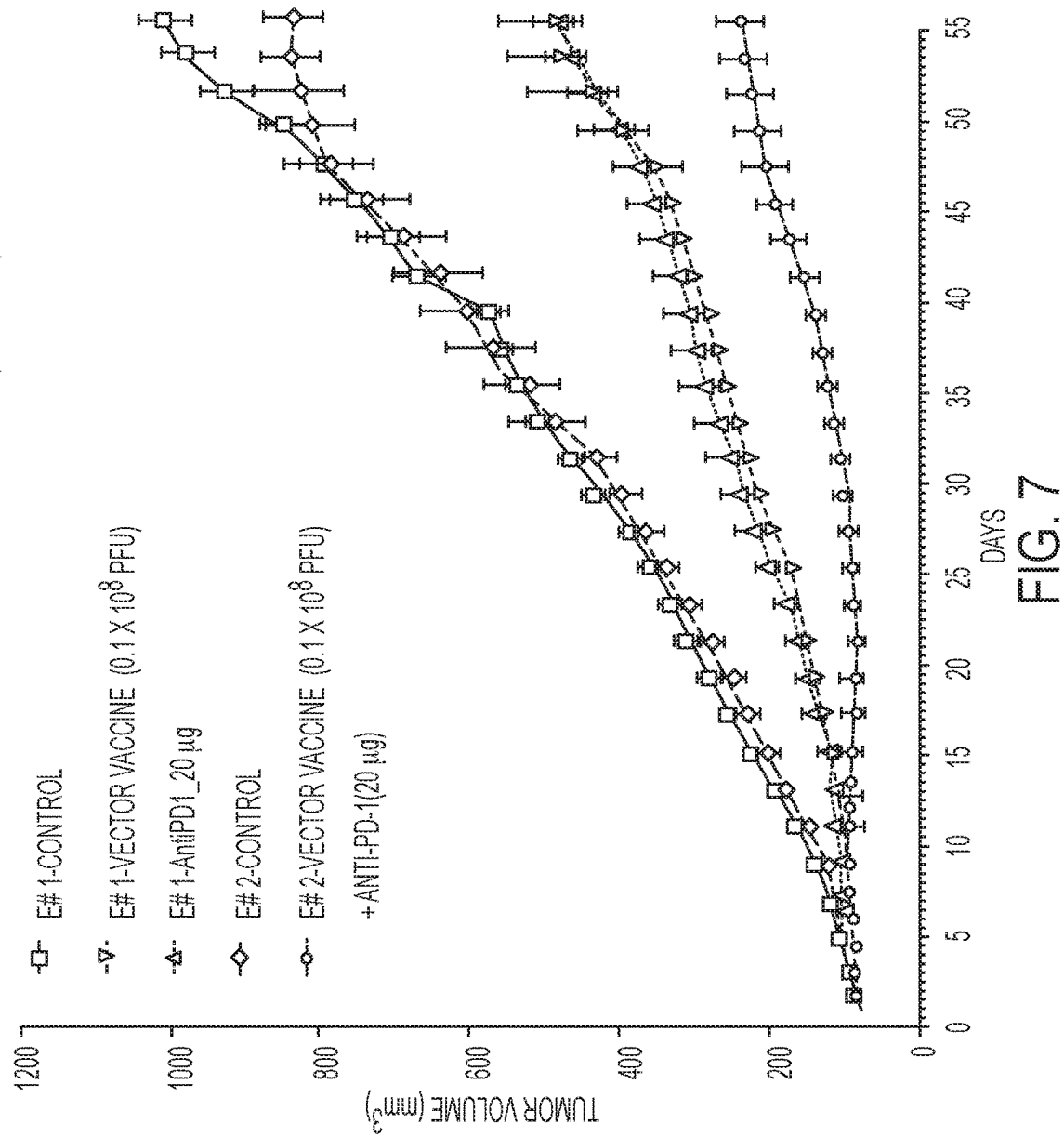

FIG. 7 graphically depicts the tumor growth kinetics of solely the two monotherapy low dose groups of Experiment 1 and the combination low dose low dose of Experiment 2 along with both controls up to day 55.

Figure 7A:
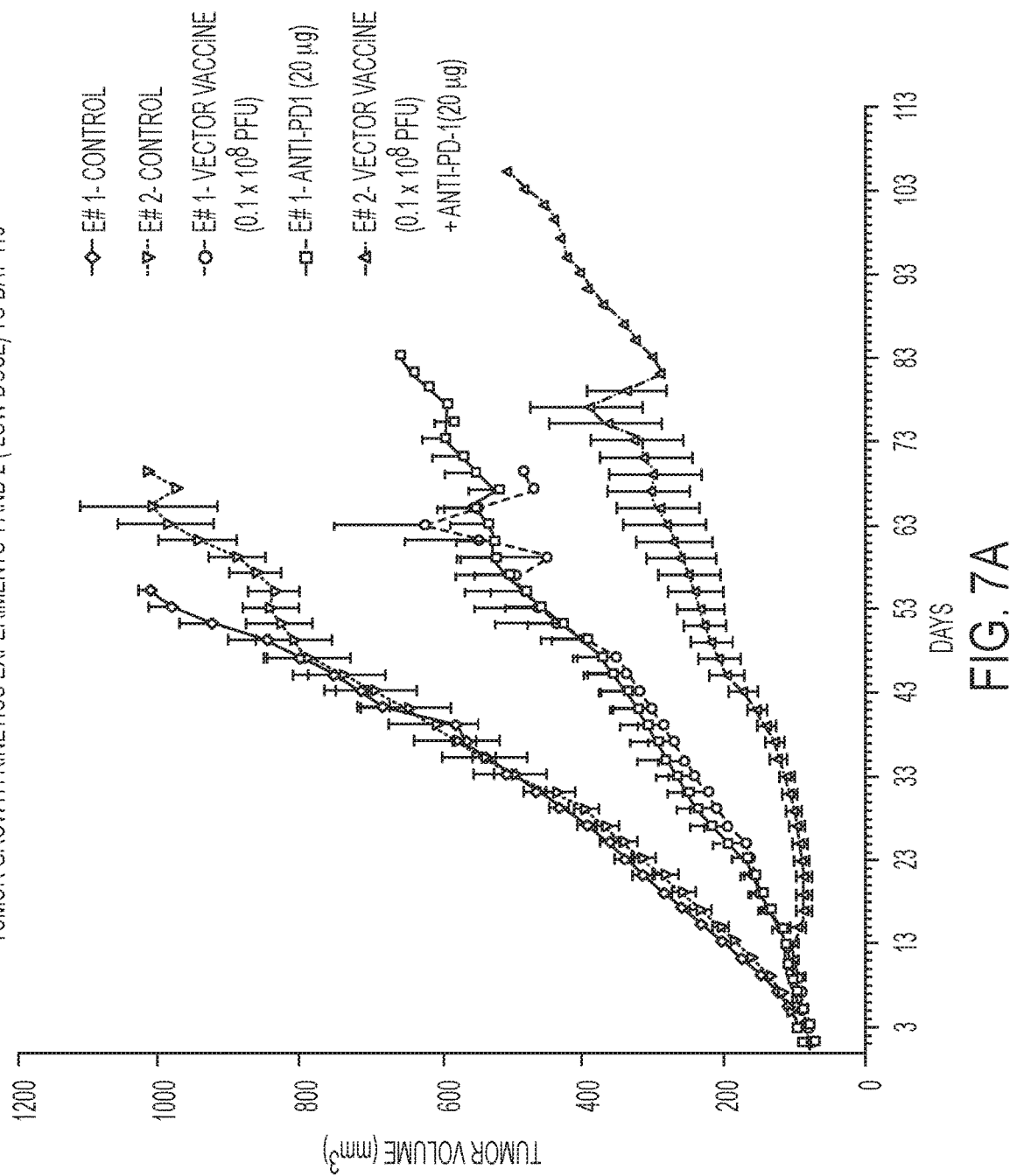

FIG. 7A graphically depicts the tumor growth kinetics of the low dose combination (of Experiment #2), and its respective monotherapies (of Experiment #1), with both controls, up to the termination of Experiment 1 at day 99, and termination of Experiment 2 at day 113.

FIG. 8 is a tabular representation of the graphical representation in FIG. 7 of solely the low dose groups and both controls for Experiments 1 and 2, and the % T/C at day 55.

Figure 9:
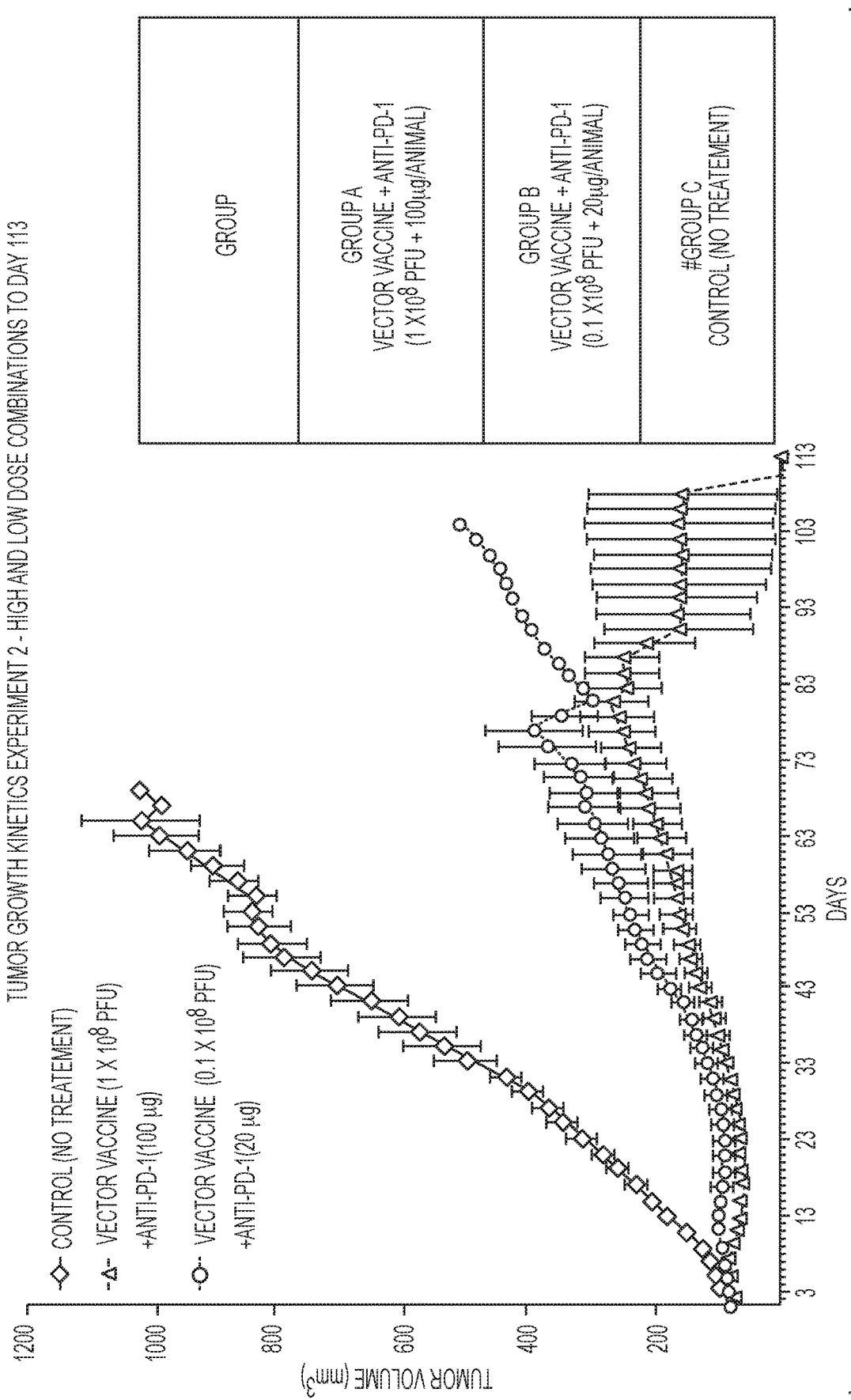

FIG. 9 graphically depicts therapeutic treatment (in graphical and tabular format) of both the high dose and low dose combinations of Vaccine and PD-1 antibody, and control for only experiment 2, suppressing tumor volume growth of E3 breast cancer in mouse model up to day 113.

Figure 10:
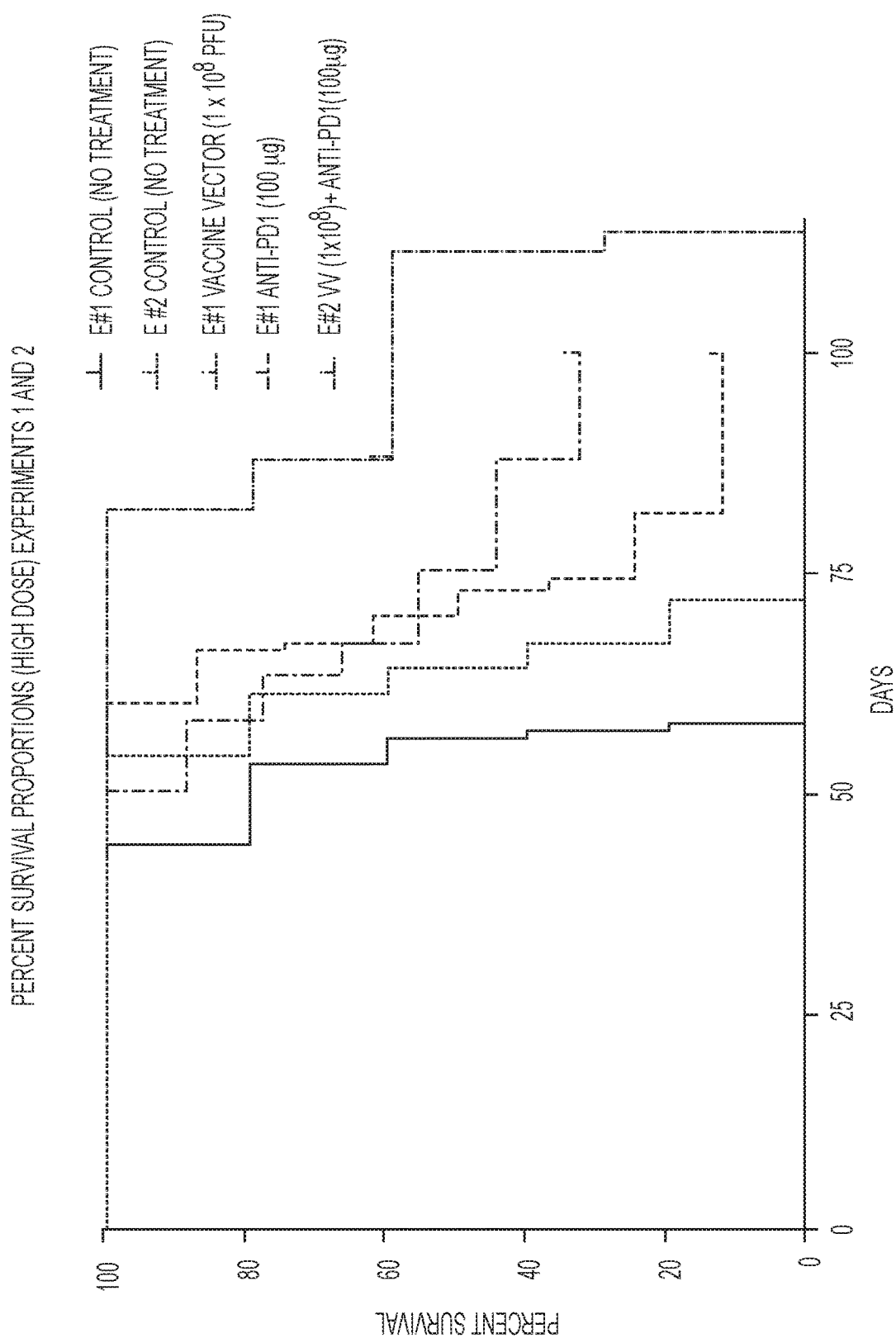

FIG. 10 is a graphical depiction of percent median survival proportions of Experiments 1 and 2, compared, for the control, monotherapy and high dose combination, for only mice that died naturally.

Figure 10A:
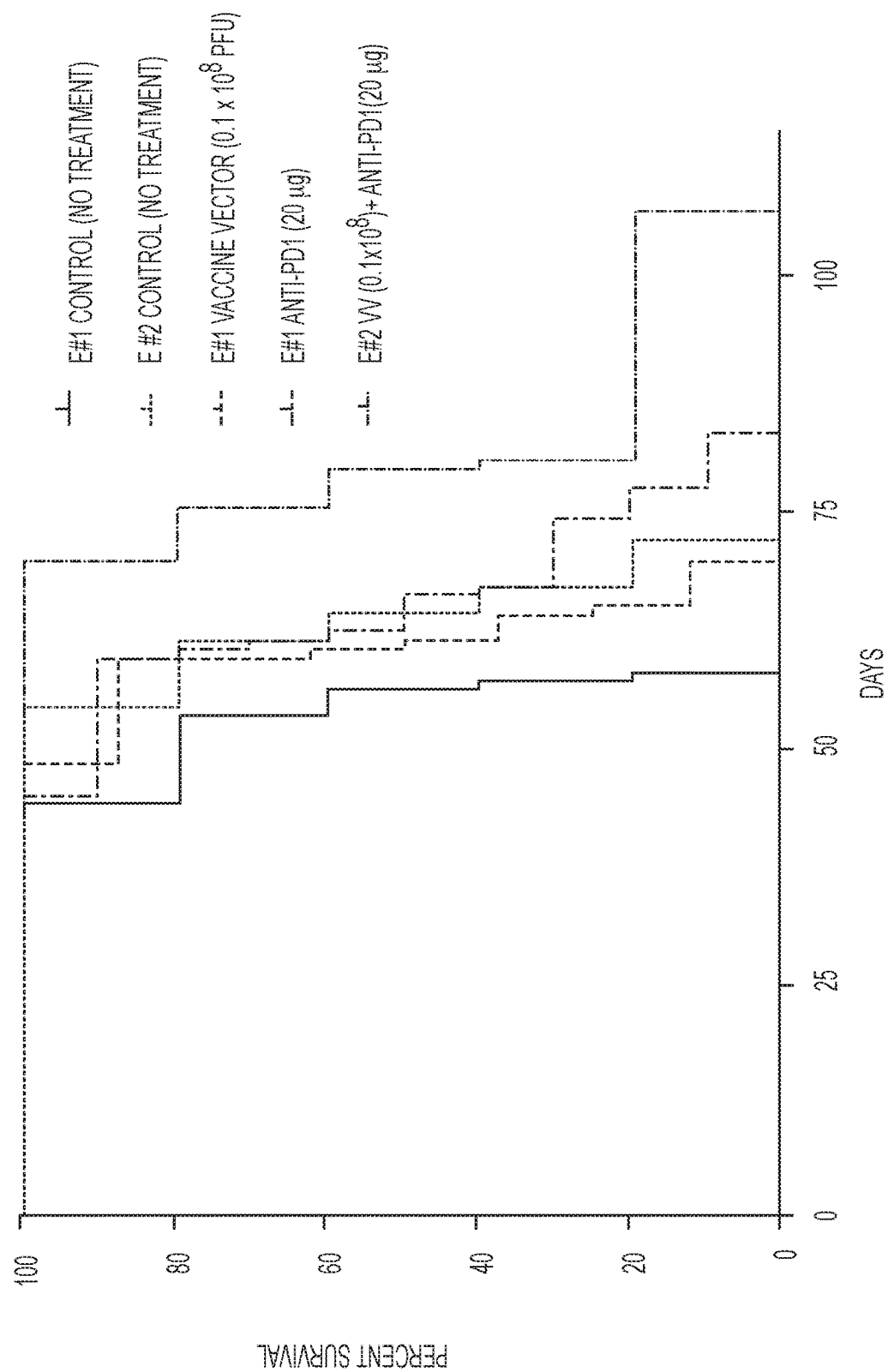

FIG. 10A is a graphical depiction of percent median survival proportions of Experiments 1 and 2, compared, for the control, monotherapy, and low dose combination for only mice that died naturally.

FIGS. 11 and 11A together depict a tabular listing by treatment group of KM (Kaplan-Meier) estimates of median survival of E3 tumor bearing mice for both controls, the four monotherapy groups, high dose combination and low dose combination, for mice that died naturally.

Figure 12:
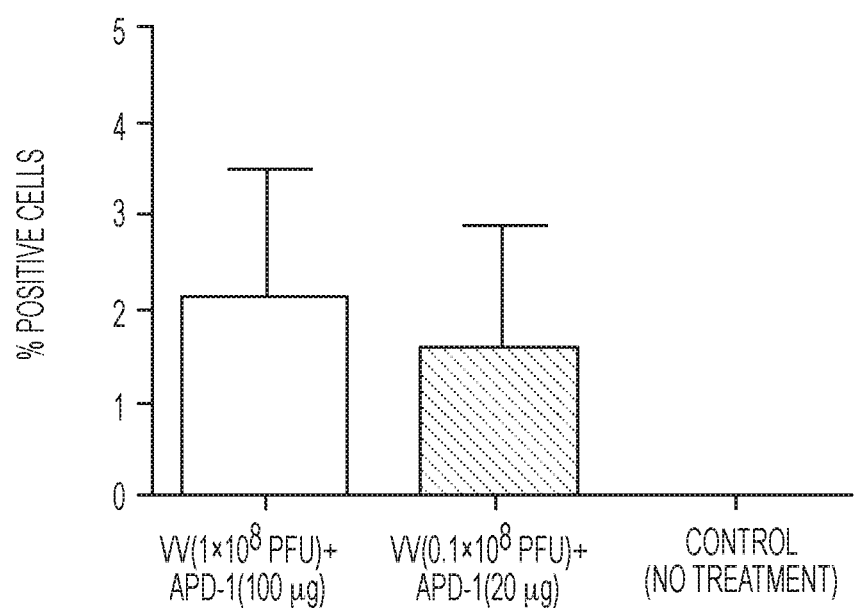

FIG. 12 is a bar graph which depicts for Experiment 2, percent cells positive for CD8 positive cells in E3 SC tumor nodules mice treated with the high dose and low dose Vaccine and PD-1 antibody combinations, versus control.

Figure 13:
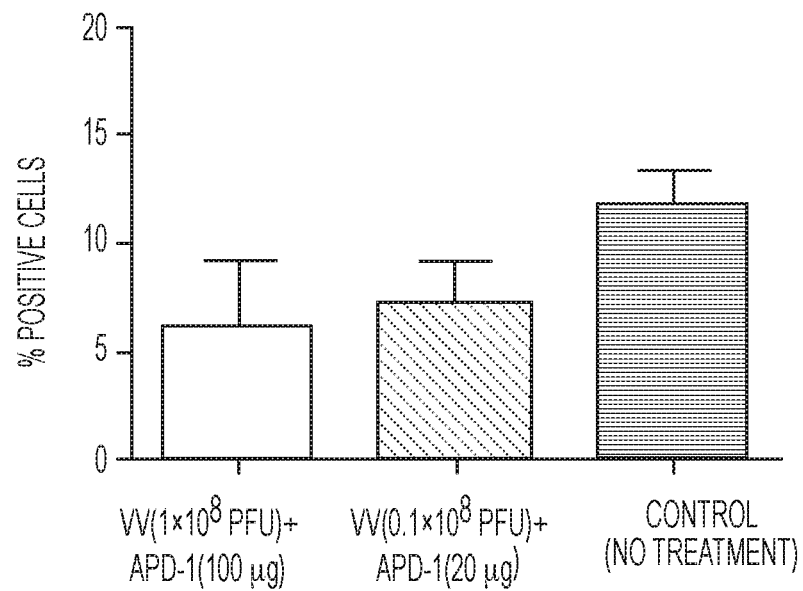

FIG. 13 is a bar graph which depicts for Experiment 2, percent cells positive for CD11b positive cells in E3 SC tumor nodules mice treated with the high dose and low dose Vaccine and PD-1 antibody combinations, versus control.

FIG. 14 is a tabular listing in Experiment 2 of the depictions in FIGS. 12 and 13, percent cells positive for CD8 and CD11b in E3 SC tumor nodules mice treated with the Vaccine and PD-1 antibody.

Figure 15:
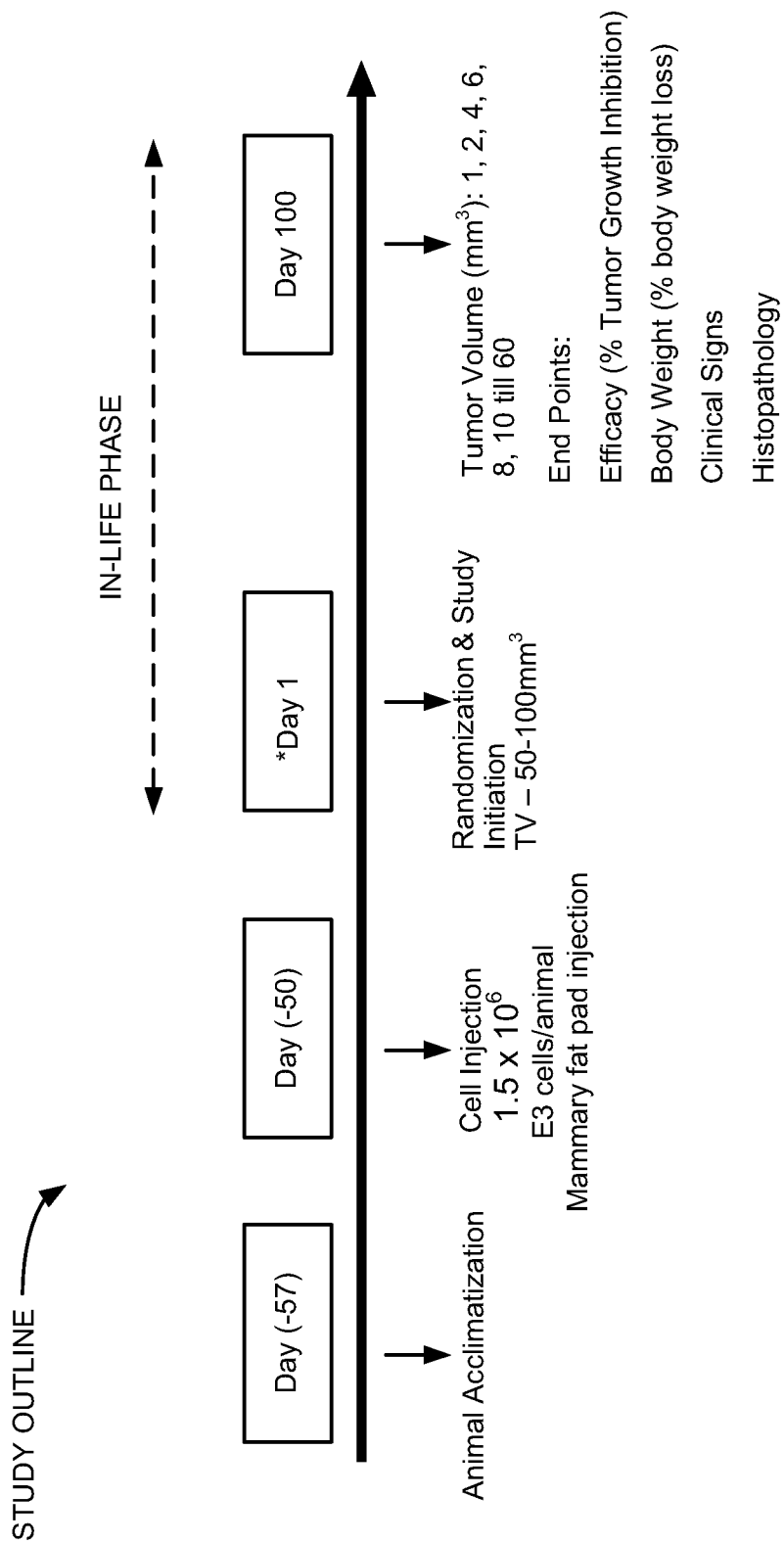

FIG. 15 illustrates a study outline timeline associated with experiments described herein.

Values in Experiments are expressed in each group as Mean+/−SEM of the 1-10 animals in Experiment 1, and the 1-5 animals of Experiment 2. Statistical analysis is carried out by Two-way ANOVA followed by Bonferroni post tests using Graph Pad Prism (Version 5).

With respect to all the graphical representations in the above referenced graphical Figures, sudden alterations in tumor growth curves is due to mortality/humane euthanasia of one or more animals from the respective grouping in the graphical figures.

Experiment 1 Evaluation/Results

Figure 1:
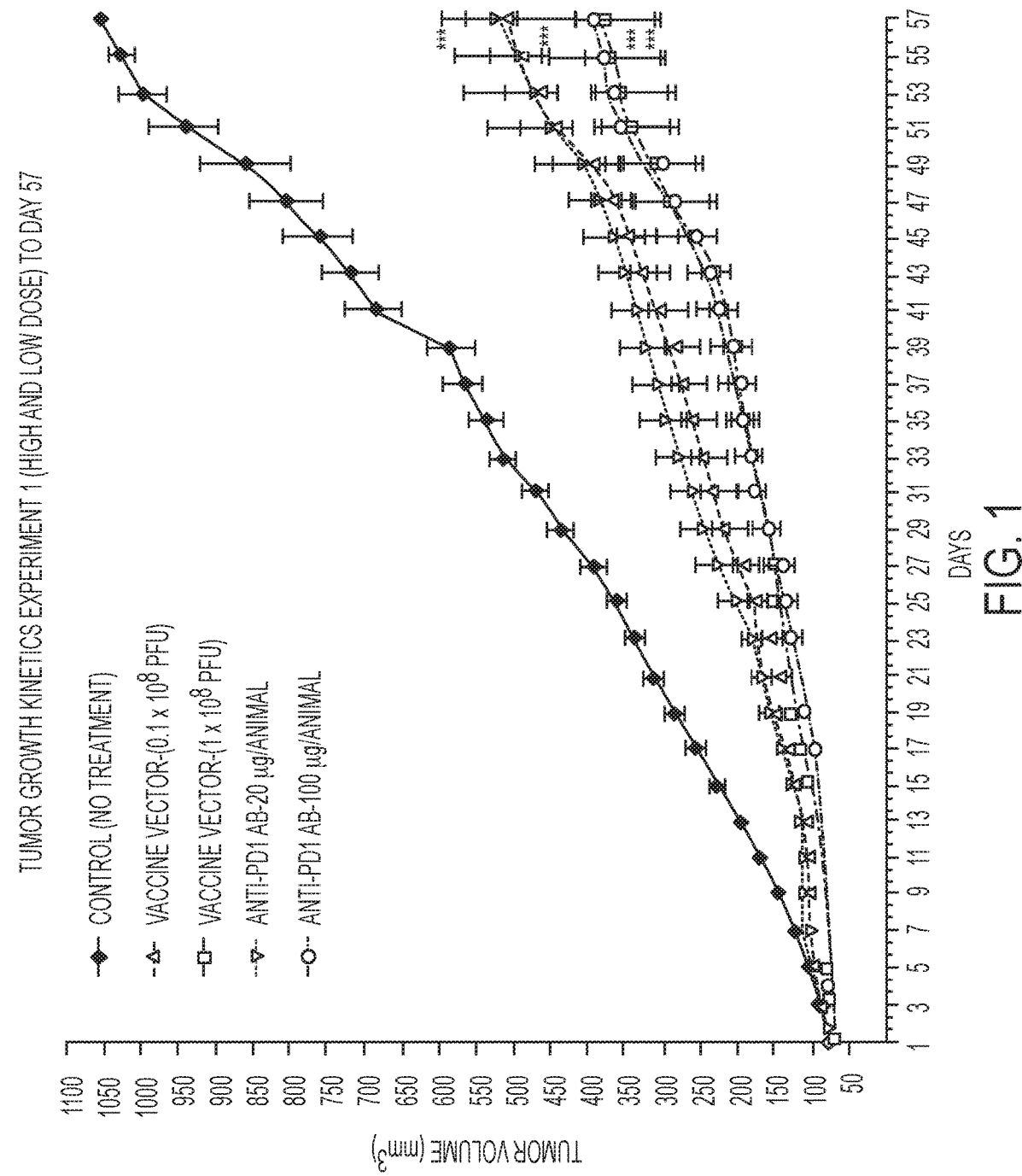

Experiment 1—Study of the Effect of the Administration of the TAA/ecdCD40L vaccine and the Anti-PD-1 Antibody as Monotherapy (each given separately) on the Growth rate of The human MUC-1 positive E3 mouse breast cancer cell line: Applicants, as a first part of the overall consideration in the instant experiment, test for the TAA/ecdCD40L vaccine platform and anti-PD-1 antibody, administering each of these, the vaccine and the antibody, to separately determine their effective therapeutic capability to suppress tumor growth when each therapy is used alone as monotherapy, and not used in combination therapy. The ability of these therapeutic treatments when separately administered to control tumor growth kinetics of the instant efficacy study, is shown in FIG. 1, where the "y" axis represents tumor growth in cubic $mm^3$ and where the "x" axis represents time in days, together, with a Table shown as FIG. 2, additionally listing the data recorded in FIG. 1 in tabular format.

As reflected in part in Tables 1 and 2, and in FIG. 15, in the specification, the mice were first injected with the E3 mammary cell line and then approximately 40 days later when the tumor growth was approximately 76 $mm^3$, the combination study began. The low dose combination group of $0.1 \times 10^8$ PFU and AB20 and high dose combination group of $1.0 \times 10^8$ PFU and AB100, were each then initiated at day 1 of experiment 2. The initial applicable vector vaccine was subcutaneously injected (high or low dose combination group), each followed by their respective (high or low dose) vector vaccine boosts at days 8, 22, 40 and 60. At the same time, the initial PD-1 antibody administration (Intraperitoneal) was also initiated at day 1 (for each the respective high dose and low dose combination group), and then their respective (high dose or low dose) boosts were administrated at days 4, 7, 10, 13, 17, 20, 23, 40 and 60. It should be noted that although the vaccine boosts were also vectors, fusion protein boosts might have been administrated subsequent to the first vector vaccine injection, as shown in Applicant's U.S. Pat. No. 8,828,957, issued Sep. 9, 2014. It should be understood, that although in the instant experiment the combination administration period was for sixty days, the combination administration period could be, for example, 120 days, 180 days, 360 days and/or 2 years. Alternatively, the combination administration of the vaccine and drug could be stopped at any one point in time, after for example, an initial sixty-day period, so that either the checkpoint inhibitor or vaccine might then be continued as monotherapy. All these possibilities might be considered, depending upon toxicity and other issues determined to be in the best interests of the subject.

As depicted, this portion of the experiment was taken over a 57-day period, and by day 55 all control animals had expired. As shown, all doses tested of the TAA/ecdCD40L vaccine and the anti-PD-1 antibody suppressed the growth of the growing tumor nodules, as compared to growth of the tumor nodules in untreated control mice shown as the control group. Experiment 1 is performed over a period of 57 days from baseline or day 1, where as previously stated baseline tumor volume on the y axis is at 76 $mm^3$ on FIG. 1.

Although other Figures will depict the experiment to continue and cover greater than a 55 day period, the 55 day period is considered to be a more representative picture of Experiment 1 in that control mice had lived until day 55, so that a comparison versus control is absent beyond the 55 day period. Nevertheless, survival and ancillary considerations were the basis for continuing the trial to beyond day 100 for Experiment 1, as well as for Experiment 2.

In Experiment 1, there were five experimental groups of 10 mice each. There was a "control" Group VI in which no treatment was given. There were two different vaccine dose groups. One vaccine dose Group I was $0.1 \times 10^8$ VP and the other vaccine dose Group II was $1.0 \times 10^8$ VP. There were two PD-1 antibody dose level groups. A first antibody Group III was treated with 20 µg, a second antibody Group IV was treated with 100 µg. As depicted in FIG. 1 and FIG. 2, each of the therapeutic monotherapy treatments (vaccine and PD-1 antibody), had the ability to slow or to inhibit tumor growth. The higher dose levels, of each vaccine and antibody, were shown to be more effective to cause slower tumor growth. Nevertheless, tumor growth still took place in all instances. In this example, when the therapeutic agents were initially administered at day 1, the baseline reading is 76 $mm^3$ as noted in FIG. 1. FIG. 1A depicts the monotherapy growth kinetics carried beyond day 55 to day 99 when Experiment 1 was terminated.

In the Table in FIG. 2, in the middle column entitled "Tumor Volume ($mm^3$)", the number "n" refers to the number of animals still alive. It is noted that a number of animals expired as a consequence of tumor growth, in this first Experiment by day 57. Based upon observation of the tumor growth curves depicted in FIG. 1, it was decided at day 40 to select from the various tumor growth curves, the combination (PD-1 dose and vaccine dose) therapies for experiment 2. On this basis, it was determined to combine the low dose vaccine $0.1 \times 10^8$ PFU and the AB20 µg as a Group A combined therapy for Experiment 2, and, in addition, to combine the high dose vaccine 1.0×10⁸ PFU and AB100 μg as a Group B combined therapy for Experiment 2. Control is designated as Group C for Experiment 2. The number of mice in each of these three groups in Experiment 2 was five mice. The mice used for Experiment 2 were from the same source and the same species and strain of mice used in Experiment 1. Accordingly, Experiment 2 commenced on day 40 of Experiment 1, while Experiment 1 continued.

Experiment 2 Evaluation/Results

Figure 3:
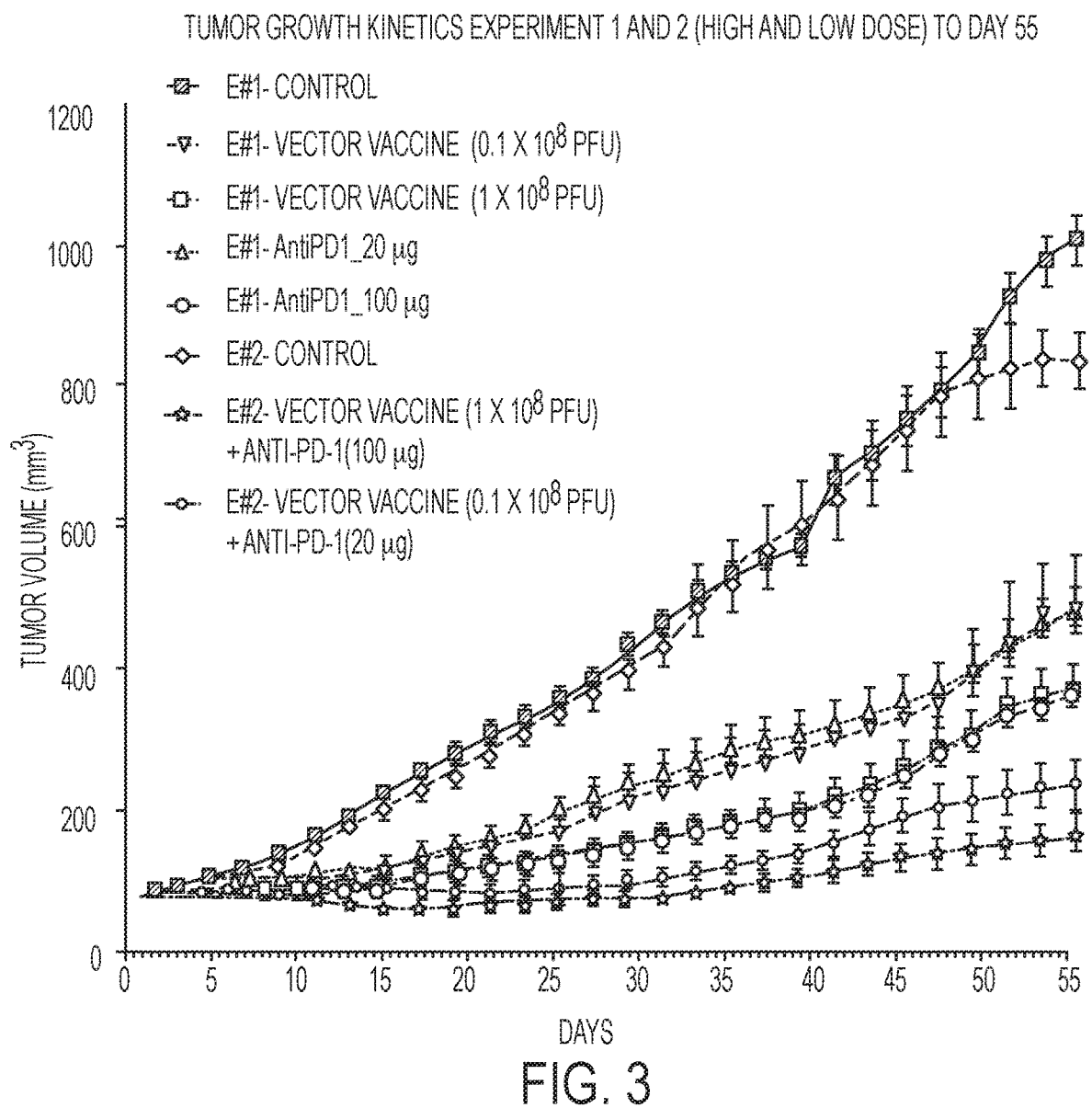
FIG. 3 is a graphical representation of tumor volume growth kinetics and of Experiment 1 and Experiment 2 up to day 55, depicting tumor volume (mm³) growth versus days.

Combined therapeutic administration trial: Tumor Growth: FIGS. 3 and 4, depict the two control curves for each Experiment 1 and 2, the vaccine and antibody monotherapy curves of Experiment 1, and the two combined therapies of high dose group (1.0×10⁸ PFU and AB100 ug), and low dose group (0.1×10⁸ and AB20 μg). When the vaccine therapy and antibody AB therapy were combined, i.e. to be administered as a combination therapy over a common time period, during which the two combined therapies were administered at the same time and/or different times, not only did the combination successfully suppress or increase the inhibition of tumor growth beyond that achieved by separate administration of the vaccine or antibody monotherapy, but the high dose vaccine and AB100 group combination, was even able to cause tumor regressions below baseline at early stages roughly between days 8 and 20, as depicted in FIG. 3.

As reflected in part in Tables 1 and 2 above, and in FIG. 15, and similar to Experiment 1, the mice were first injected with the E3 mammary cell line and then approximately forty days later when the tumor growth was approximately 75 mm³ the study was initiated by subcutaneously injecting the vector vaccine and antibody combinations for each animal group A and B (high and low dose combinations), followed by their boosts (high and low dose as appropriate for separate groups of animals), at days 8, 22, 40 and 60 for the respective vector vaccine dose level and days 4, 7, 10, 13, 17, 20, 23, 40 and 60 for the respective PD-1 antibody dose level. It should again be noted that although the vaccine boosts were also vectors, fusion protein boosts could have been administrated subsequent to an initial vector vaccine injection, as shown in Applicant's U.S. Pat. No. 8,828,957. As depicted, the combined therapies were both administered on days 1, 40 and 60. The initial doses were administered on the same day and the two last doses were administered on the same days (days 40 and 60). The remaining therapy boosts (vaccine and antibody) although administered within a common time frame were each administered on different days.

The tabular listing in FIG. 4 depicts the results of FIG. 3 at day 55 of Experiment 2 compared with day 55 of Experiment 1, including controls of Experiment 1 and 2 (Group VI and Group C), and the separate monotherapy administrations of vaccine and antibody for both high dose and low dose (Groups I-IV), and the combination therapy for each (Groups A and B). From the tumor volume column in FIG. 4, representing tumor volume at day 55, and from the percentage of T/C (tumor volume over control volume at day 55), the advantage of the combined therapies is shown to be more than additive. In fact, in each instance, high dose and low dose, the increase was close to or greater than a two-fold increase. For example, in the right-hand column in FIG. 4, the high dose % T/C (percentage of tumor growth over control growth) was 20% whereas the high dose monotherapies (0.1×10⁸ PFU vaccine and AB20) were respectively 36% and 37%. Looking at it from a different perspective and slightly earlier in time, at day 43 of Experiment 1 and day 43 of experiment 2, from approximate measurements for each, the monotherapy Experiment 1 and the combined Experiment 2, the monotherapy high dose vaccine tumor volume mean was at 228 mm³, the monotherapy AB100 high dose tumor volume mean was 237 mm³, whereas the combined high dose tumor volume mean was at 116 mm³. Although the latter tumor suppression capability of the combined therapies was a hopeful goal of the experiment, nevertheless, because of many of the reasons advanced in this specification, it was not anticipated, and the extent of the suppression was surprising.

Yet another example, at day 43 of Experiment 1 and day 43 of Experiment 2, from approximate measurements for each the monotherapy Experiment 1 and the combined Experiment 2, the monotherapy low dose vaccine tumor volume mean was at 323 mm³, the monotherapy AB20 low dose tumor value mean 343 mm3, and the combined low dose tumor volume mean was at 153 mm³.

FIGS. 5 and 6 provide the comparison of the high dose combination alone in Experiment 2 as compared with the separate high dose vaccine and antibody monotherapy administrations in Experiment 1. FIG. 5A depicts the high dose graphics (for each monotherapy and combination therapy) extended out to day 113 when Experiment 2 was terminated. Similarly, out to day 55, FIGS. 7 and 8 provide the comparison of the low dose combination in Experiment 2 as compared with the separate low dose vaccine and antibody monotherapy administrations in Experiment 1. FIG. 7A depicts the low dose graphics extended out to day 113 when Experiment 2 was terminated. FIG. 9 additionally depicts the growth kinetics of the low and high dose combination therapies, compared with the control for experiment 2, where Experiment 2 was continued to day 113, for survival considerations, and Applicants continued to find that the high dose combination as depicted, was a more preferred combination depicting significantly better growth inhibition.

Combined Therapeutic Administration: Survival: As to the survival of the animals in the combined trial for the high dose combination, as shown in the FIG. 10, it was also surprising and unexpected that the high dose combination treated mice had survived for a considerable period, as listed in FIG. 11A where, using the Kaplan-Meier estimates of median survival of E3 tumor bearing mice, the KM median survival of the high dose combination Group A was 99.5, exceeding all other groups by a considerable margin. FIGS. 10A and 11 (KM median survival table), depict survival for the low dose combination therapy.

As part of the experiment, quantitative evaluation for CD8 and CD11b positive cells were conducted after performing immunohistochemistry of tumor slides of all treatment groups to assess the pathological changes observed. A protocol was developed for each the CD8 and CD11b staining. In each case 300 cells from three different microscopic fields for each slide were counted for CD8 and CD11b markers Percent positive cells were calculated from 300 cells for CD8 and CD11b markers.

As depicted in FIG. 12, in Experiment 2, the combined therapeutic treatment with the vaccine therapy and PD-1 antibody therapy, in each case, clearly induced an increase in the percentage of positive CD8 effector T cells compared with control. The CD8 percent positive cells was slightly higher in the high dose combination compared to low dose combination. No positive CD8 cell was observed in the control (no treatment) group. The error bars for the higher dose combination do not overlap with the error bars of the untreated control mice. Thus, this result depicts that the vaccine therapy, when combined with the PD-1 antibody therapy, promotes the entry of CD8 effector T cells into the cancerous tumor tissue, and thus it is believed to convert the cold non-inflamed cancerous tumor tissue to more highly responsive cancerous tumor tissue.

At the same time, as shown in FIG. 13, the treatment with the higher dose combinations of antibody and vaccine therapy induced a decrease in the percentage of cells which are positive for CD11b as compared with control. The percent positive cells for CD11b were slightly higher in the low dose combination treatment compared to the high dose combination treatment. The CD11b positive cells were maximum in the control (no treatment) group. CD11b is a marker for myeloid inhibitory cells. Thus, the TAA/ecdCD40L vaccine—PD-1 antibody combination treatment changed the microenvironment in the E3 tumor nodules as depicted in FIG. 13. Accordingly, the treatment with the combination of the TAA/ecdCD40L vaccine with the PD-1 antibody, is believed to have converted the immunoregulatory environment from inhibitory to immuno-stimulatory. This is further depicted in the tabular listing on FIG. 14, showing increases in the percentage of CD8 effector T cells and decreases in the percentage of CD11b positive cells, compared with control.

The decreases in the percentage of CD11b positive cells (which includes a cell subset known as monocytic myeloid-derived suppressor cells or MDSC) is a positive indicator, since they are known to inhibit T cell proliferation and activation. Under chronic inflammatory conditions (viral and bacterial infections) or cancer, myeloid differentiation is skewed towards the expansion of MDSCs. These MDSCs infiltrate inflammation sites and tumors, where they stop immune responses by suppressing or inhibiting T cells and NK cells (natural killer cells), for example. MDSCs also accelerate angiogenesis, tumor progression and metastasis through the expression of cytokines and factors such as TGF-beta. Clinical and experimental evidence has shown that cancer tissues with high infiltration of MDSCs are associated with poor patient prognosis and resistance to therapies. Therefore, they have become a key therapeutic target, and in the present case provide additional support for the combination therapy to be a significant improvement over the monotherapies.

Although not wishing to be bound by any theory, based upon the results of the Experiment, it is it is believed that non-inflamed or cold tumors (low level of infiltrating CD8 effector T cells), which do not respond to the non-targeted anti PD-1 antibody therapy, become hot tumors that are responsive to the PD-1 antibody therapy with the combination targeted vaccine therapy, and that TAA/ecdCD40L, increases TAA specific CD8 T cells in TAA subcutaneous tumor nodules in mice. It is also believed that due to the targeted and non-targeted approaches being together with the different types of therapy administration (subcutaneous and intra-peritoneal), this yields the desired effect of having a significant therapeutic effect in terms of both efficacy and survival.

In summary, notwithstanding the foregoing, it is submitted that the overall experiment results evidence that the Ad-sig-hMUC-1/ecdCD40L vaccine therapy, in addition to its own capability to induce a therapeutic response, acts as a catalyst and/or stimulus, to enable an increase in the overall therapeutic response rates to the PD-1 antibody therapy including an increase in survival time to prolong life. Clearly, there is an interaction and/or co-operation of the two therapies to produce a surprisingly significant improvement in the unpredictable field of cancer immunotherapy, and, it is submitted to be a novel approach in the treatment of cancer patients. Accordingly, Applicants' invention provides for a vaccine therapy, that when combined with a PD-1 antibody therapy, is believed to exhibit a dual therapeutic capability.

It should be understood, of course, that additional vaccine boosts, additional antibody boosts and/or other additive form(s) of therapy, might be additionally administered within and/or outside of the above identified common time period which happened to be selected for 60 days for experimental purposes. Also, a common time period for application of the combination therapy might be 90, 120 or even 180 days, or more. The combination therapy for any one or more patients might last for as long as the time period currently prescribed for administering solely checkpoint inhibitor antibody therapy, which for many has been a period of two years. There also may be dose variations. For example, although the initial vaccine dose may be a vector, the boosts could be fusion proteins. Other variations might include dose boosts to be at a different dose level. For example, the initial antibody dose may be 100 mg, successive antibody boosts might be at 80 mg. The purpose of the above experimentation was to determine whether the combination of the TAA/ecdCD40L vaccine and antibody therapy if applied together within a common time frame, might produce some form of interaction and/or synergism, and/or act as a catalyst, without producing serious side effects, that would generate an enhanced therapeutic and/or survival effect for cancer patients.

Some Conclusions of the Experimental Study

1. The combination of the vaccine and PD-1 antibody has the effectiveness to suppress growth of E3 tumor cells by at least a factor of two-fold over either therapy alone.
2. The combination of the two therapies provides one or more benefits that cannot be obtained by each of the therapies used as a monotherapy.
3. Each one of the combined therapies provides for a meaningful contribution to materially enhance the overall effect (efficacy, duration and/or safety) of the combination.
4. Ad-sig-hMUC-1/ecdCD40L treated mice (Group II) survive longer (71 days) than untreated control mice (Groups VI or C, by respectively 56 days and 62.5 days).
5. Anti-PD-1 treated mice (Group IV) survive longer (75 days) than untreated control mice (56 days or 62.5 days).
6. Mice treated with the combination of TAA/ecdCD40L vaccine and antibody (Group A) survive longer (99.5 days) than mice treated with the monotherapy vaccine (71 days) or monotherapy antibody (75 days) alone.
7. Treatment with the TAA/ecdCD40L vaccine and anti-PD-1 antibody combination, induces an increase in CD8 effector T cells and additionally promotes a decrease of myeloid-derived suppressor cells (MDSCs) inhibitory cells in tumor nodules thereby increasing the immunoregulatory environment from inhibitory to immune stimulatory.
8.

Multiple Advantages

As evidenced from the Applicants' experiment, there are a number of significant advantages believed to have been uncovered in using the combined therapeutic approach of the Ad-sig-hMUC-1/ecdCD40L vaccine together with the checkpoint inhibitor (for example, PD-1) in the manner described in the specification as, for example:

The TAA/ecdCD40L vaccine therapy, together with the checkpoint inhibitor antibody therapy, increases the number of antigen specific T cells that traffic into the tumor nodule(s) causing enhanced efficacy, with reduced destruction of normal tissue (non-cancerous tumors) in a subject, due to the antigen targeting vaccine and use of a possibly reduced dose level of antibody and/or administration of doses over a shorter period of time compared to current conventional or standard period of PD-1 therapeutic administrations. Alternatively, a greater population of cancer patients might be successfully treated by the combination.

Longer survival period along with enhanced efficacy can be achieved.

Reduction of toxicity issues to patients without diminishing clinical efficacy by using lower dose levels and/or number of antibody administrations/infusions, in combination with the administration of the therapeutic TAA/ecdCD40L vaccine.

Reduction of dose frequency in need of a patient being administered with checkpoint inhibitor therapy which is currently administered every two to three weeks over a two-year period, which might result in a reduction of cost associated with antibody administration, without diminishing efficacy.

Employment of the TAA/ecdCD40L vaccine platform in combination with a checkpoint inhibitor, may benefit the patient through survival over a longer period of time, as the vaccine therapy has been previously shown to additionally provide for an immuno-therapeutic memory.

Increases the additional effectiveness of the overall treatment by a) targeting the tumor antigen of interest and b) expanding the percentage of patients that respond to the combined immunotherapy as opposed to the percentage of patients that would respond to the vaccine monotherapy alone or antibody monotherapy alone.

The vaccine therapy, when combined with the PD-1 antibody therapy, is believed to convert the cold non-inflamed cancerous tumor tissue to more highly responsive hot or inflamed cancerous tumor tissue.

The above multiple advantages underscore that the interaction of the two therapies when used in combination at appropriate dosage levels, produces an overall synergistic and/or complementary effect that is greater than the sum of the two therapies when each is used alone as a monotherapy.

The invention claimed is:

1. A method of treating cancerous tumor tissue in a patient comprising an immuno-therapeutic combination to induce a synergistic tumor suppressive response in the patient, wherein said combination is administered through at least two distinct immunotherapeutic treatments, comprising an antigen non-specific PD-1 or antibody treatment and an expression vector Ad-sig-hMUC-1/ecdCD40L antigen specific vaccine treatment, administered over a common time period, comprising:

administering an initial antibody treatment at a second effective amount and followed by administering a plurality of antibody boost treatments at the second effective amount, and administering an initial vaccine treatment at a first effective amount followed by administering a plurality of vaccine boost treatments at the first effective amount, whereby upon being administered over said common time period said two distinct immunotherapeutic treatments biologically interact with each other to both increase patient survival and increase the magnitude of an anti-tumor immune response and convert cold tumor tissue having a low level of infiltrating CD8 T lymphocyte cells that are non-responsive to antibody therapy to hot tumor tissue having an infiltration of MUC-1 antigen specific CD8 T cell lymphocyte cells making said cold tumor tissue responsive to antibody therapy treatment, and resulting in a significant increase in the suppressive effect over both the antibody treatment and the vaccine treatment administered alone as monotherapy, wherein a plurality of said initial and boost treatments are administered within said common time period of a minimum of approximately sixty days to enable said immuno-therapeutic biological interaction of said combination to take effect.

2. A method according to claim 1 wherein, the first effective amount for the vaccine treatment ranges from approximately $0.1 \times 10^{11}$ vector
particles to $1.0 \times 10^{11}$ vector particles and the antibody treatment ranges from approximately 20 mg to 250 mg.

3. The method of claim 1, wherein at least one antibody treatment is administered for each vaccine treatment, during said common time period.

* * * * *